US010468722B2

(12) United States Patent
Jones et al.

(10) Patent No.: US 10,468,722 B2
(45) Date of Patent: Nov. 5, 2019

(54) ORGANIC SYNTHESIS APPLICATIONS OF NON-AQUEOUS FLUORIDE SALT SOLUTIONS

(71) Applicants: CALIFORNIA INSTITUTE OF TECHNOLOGY, Pasadena, CA (US); THE REGENTS OF THE UNIVERSITY OF CALIFORNIA, Oakland, CA (US)

(72) Inventors: Simon C. Jones, Whittier, CA (US); Victoria K. Davis, Santa Clarita, CA (US); Christopher M. Bates, Monrovia, CA (US); Nebojsa Momcilovic, Vienna, VA (US); Brett M. Savoie, Pasadena, CA (US); Michael A. Webb, Pasadena, CA (US); Thomas F. Miller, III, South Pasadena, CA (US); Robert H. Grubbs, South Pasadena, CA (US); Jennifer M. Murphy, Los Angeles, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 39 days.

(21) Appl. No.: 15/229,026

(22) Filed: Aug. 4, 2016

(65) Prior Publication Data

US 2017/0057908 A1 Mar. 2, 2017

Related U.S. Application Data

(60) Provisional application No. 62/200,998, filed on Aug. 4, 2015.

(51) Int. Cl.

*C07C 209/68* (2006.01)
*H01M 10/0568* (2010.01)
*H01M 10/0525* (2010.01)
*H01M 10/0569* (2010.01)

(52) U.S. Cl.

CPC ....... *H01M 10/0568* (2013.01); *C07C 209/68* (2013.01); *H01M 10/0525* (2013.01); *H01M 10/0569* (2013.01); *H01M 2300/0025* (2013.01)

(58) Field of Classification Search

None

See application file for complete search history.

(56) References Cited

U.S. PATENT DOCUMENTS 4,052,539 A 10/1977 Shropshire et al.
4,510,256 A 4/1985 Zones
5,876,685 A 3/1999 Krulik et al.
6,306,540 B1 10/2001 Hiroi et al.
6,852,446 B2 2/2005 Barbarich
7,169,333 B2 1/2007 Dobler et al.
7,255,966 B2 8/2007 Kim et al.
7,744,851 B2 6/2010 Dimagno et al.
8,168,831 B2 5/2012 Otsuki et al.
8,178,237 B2 5/2012 Ugawa
8,377,586 B2 2/2013 Yazami
8,658,309 B2 2/2014 Yazami
9,045,579 B2 6/2015 Xia et al.
9,166,249 B2 10/2015 Darolles et al.
9,331,360 B2 5/2016 Weiss et al.
9,382,387 B2 7/2016 Xia et al.
9,453,943 B2 9/2016 Miyake et al.
2008/0019906 A1 1/2008 Dimagno et al.
2009/0310222 A1 12/2009 Pudleiner et al.
2010/0092755 A1 4/2010 Pudleiner et al.
2010/0305368 A1 12/2010 Grubbs et al.
2011/0076572 A1 3/2011 Amine et al.
2011/0143219 A1 6/2011 Weiss et al.
2012/0164541 A1 6/2012 Darolles et al.
2015/0303514 A1 10/2015 Nakamoto et al.
2016/0024244 A1 1/2016 Xia et al.
2016/0043440 A1 2/2016 Nakamoto et al.
2016/0285129 A1 9/2016 Nakamoto et al.
2016/0289392 A1 10/2016 Grubbs et al.
2016/0356923 A1 12/2016 Miyake et al.
2017/0018795 A1 1/2017 Nakamoto et al.
2017/0018801 A1 1/2017 Grubbs et al.
2017/0033359 A1 2/2017 Ogumi et al.
2017/0062874 A1 3/2017 Jones et al.

FOREIGN PATENT DOCUMENTS

CN 1535944 10/2004
CN 103992275 * 8/2014

(Continued)

OTHER PUBLICATIONS

English Machine Translation of Shi et al. 2014 (CN 103992275).*

(Continued)

*Primary Examiner* — Sudhakar Katakam
*Assistant Examiner* — Jennifer C Sawyer
(74) *Attorney, Agent, or Firm* — Leydig, Voit & Mayer, Ltd.

(57) ABSTRACT

Processes and reaction mixtures including non-aqueous solvent mixtures are presented. Non-aqueous solvent mixtures including fluoride salt and non-aqueous solvent combinations are provided that possess high fluoride ion concentrations useful for a range of applications, including organic synthesis. Further non-aqueous solvent mixtures are provided including a salt possessing a non-fluoride anion and a non-aqueous solvent that, when contacted with aqueous fluoride-containing reagents, extract fluoride ions to form non-aqueous fluoride-ion solutions possessing high fluoride-ion concentrations. The salts include an organic cation that does not possess a carbon in the β-position or does not possess a carbon in the β-position having a bound hydrogen. This salt structure facilitates its ability to be made anhydrous without decomposition. Example anhydrous fluoride salts include (2,2-dimethylpropyl)trimethylammonium fluoride and bis(2,2-dimethylpropyl)dimethylammonium fluoride. The combination of these fluoride salts with at least one fluorine-containing non-aqueous solvent (e.g., bis(2,2,2-trifluoroethyl)ether; (BTFE)) promotes solubility of the salt within the non-aqueous solvents.

22 Claims, 13 Drawing Sheets

(56) References Cited

FOREIGN PATENT DOCUMENTS

| | | |
|---|---|---|
| DE | 102006015787 | 4/1985 |
| EP | 1 718 713 | 11/2006 |
| EP | 2 133 202 | 12/2009 |
| EP | 2 157 133 | 2/2010 |
| JP | 2006-221973 | 8/2006 |
| JP | 2012-089704 | 5/2012 |
| WO | WO 1992/020446 | 11/1992 |
| WO | WO 2001/085869 | 11/2001 |
| WO | WO 2011/072166 | 6/2011 |
| WO | WO 2012/087414 | 6/2012 |
| WO | WO 2015/093272 | 6/2015 |
| WO | WO 2015/098766 | 7/2015 |
| WO | WO 2015/146265 | 10/2015 |

OTHER PUBLICATIONS

Abboud et al. (1991) "Critical Compilation of Scales of Solvent Parameters. Part I. Pure, Non-Hydrogen Bond Donor Solvents," Pure Appl. Chem, 71:645-718.

Brown et al. (1953) "Chemical effects of steric strains. VII. Strained homomorphs. III. Steric strains as a factor in the soivoiytic reactions of neopentyidimethyi- and dineopentyimethyi-carbinyi chiorides," Journal of the American Chemical Society. 75:10-14.

Brown et al. (1953) "Chemical effects of steric strains. VIII. Strained homomorphs. IV. Neopentyitrimethyiammonium ion as a strained homomorph; the rates of reaction of neopentyldimethylamine with aikyi iodides," Journal of the American Chemical Society. 75:14-16.

Brown et al. (1953) "Stereochemistry. XIX. Strained homomorphs. I. General summary," Journal of the American Chemical Society. 75:1-6.

Christe et al. (Oct. 1990) "Syntheses, properties, and structures of anhydrous tetramethy !ammonium fluoride and its 1: 1 adduct with trans-3-amino-2-buteneitrile," J. Am. Chern. Soc. 112:21.7619-7625.

Edson et al. (2012) "Hydroxide based decomposition pathways of alkytrimethylammonium cations," Journal of Membrane Science. 399-400:49-59.

Eyal et al. (1989) "Hydrofluoric Acid Extraction by TBP and by Amines: I. A Critical Review of the HF-H2O-Extractant System," Solvent Extraction and Ion Exchange. 7(6):951-969.—Abstract Provided Only.

Ford (1973) "Synthesis of trineopentylamine," Journal of Organic Chemistry. 38:20.3614-15.

Gordin et al. (May 15, 2014) "Bis(2,2,2-trifluoroethyl) Ether as an Electrolyte Co-Solvent for Mitigating Self-Discharge in Li/S Batteries," ACS App. Materials & Interfaces, 6.11. 8006-8010.

Gross et al. (2002) "19F-NMR solid state investigations of monovalent alkali metal fluorides and tetra-alkylammonium fluorides," Journal of Fluorine Chemistry. 115:2. 193-199.

Grovenstein et al. (1964) "Carbanions. VII. Cleavage of 2,2-dimethylpropyl-2,2,2-triphenylQthyl-, and 3,3,3-triphenylpropyltrimethylammonium iodides by sodium in liquid ammonia," Journal of the American Chemical Society. 86:5.854-61.

Gutmann (1976) "Solvent effects on the reactivities of organometallic compounds," Coord. Chem. Rev., 18:225-255.

Ingold et al. (1933) "Influence of poles and polar linkings on the course pursued by elimination reactions, XI, Decomposition of quaternary ammonium hydroxides containing the tert-butylcarbinyl group," Journal of the Chemical Society. 67-8.

Iwai et al. (1963) "Acetylenic compounds. XXXIV. Rearrangement of propargylammoniumhalide derivatives," Chemical & Pharmaceutical Bulletin. 11:12.1556-63.

Long et al. (2012) "Hydroxide Degradation Pathways for Substituted Trimetliylammonium Cations: A DFT Study," Journal of Physical Chemistry. 115:17.9419-9426.

Mahjoub (1995) "Reactions of the 'naked' fluoride ion; syntheses and structures of SeF62- and BrF6-," Chemistry—A European Journal. 1:4.261-5.

Manecke et al. (1986) "Encyclopedia of Polymer Science and Engineering, 2nd Edition," John Wiley. 5:725-755.

Marino et al. (2015) "Alkaline Stability of Quaternary Ammonium Cations for Alkaline Fuel Cell Membranes and Ionic Liquids," ChemSusChem. 8:3.513-523.

Pine et al. (1970) "Stevens rearrangements of N,N,N-trimethylneopentylammonium iodide," Journal of Organic Chemistry. 35:11.3663-6.

Sharma et al. (Jun. 1983) "Instability of anhydrous tetra-n-alkylammonium fluorides," J. Org. Chern., vol. 48, No. 12, pp. 2112-2114.

Stevens et al. (1941) "Mechanism of elimination reactions. I. The decomposition of quaternary ammonium bases and of xanthate esters," Journal of the American Chemical Society. 63:3132-6.

Weng et al. (Jan. 20, 2013) "Ultrasound Assisted Design of S/C Cathodes with Partially Fluorinated Ether Electrolytes for Highly Efficient Li/S Batteries," Advanced Materials, 25.11. 1608-1615.

White et al. (1961) "The synthesis and certain reactions of nitroalkanes and nitro amines," United States Department of Commerce, Office of Technical Services. PB Report. 156.069.8.

Wynn et al. (Nov. 1984) "The solubility of alkali-metal fluorides in non-aqueous solvents with and without crown ethers, as determined by flame emission spectroscopy," Talana, vol. 31, No. 11, pp. 1036-1040.

Zhang et al. (1995) "Fluorocarbonate, [FC02]—: preparation and structure," Angewandte Chemie. 34:17.1858-60.

International Search Report with Written Opinion corrsponding International Patent Application No. PCT/US2016/045645, dated Jun. 16, 2017.

Written Opinion corrsponding International Patent Application No. PCT/US2016/045617, dated Jun. 15, 2017.

U.S. Appl. No. 12/680,316, filed Aug. 11, 2010, 2010/0305368, Dec. 2, 2010.

U.S. Appl. No. 13/800,646, filed Mar. 13, 2013, 2013/0324666, Dec. 5, 2013, U.S. Pat. No. 9,382,387, Jul. 5, 2016.

U.S. Appl. No. 13/801,710, filed Mar. 13, 2013, 2013/0296491, Nov. 7, 2013, U.S. Pat. No. 9,045,579, Jun. 2, 2015.

U.S. Appl. No. 13/930,400, filed Jun. 28, 2013, 2014/0011958, Jan. 9, 2014, U.S. Pat. No. 9,453,943, Sep. 27, 2016.

U.S. Appl. No. 14/698,520, filed Apr. 28, 2015, 2016/0024244, Jan. 28, 2016.

U.S. Appl. No. 15/065,291, filed Mar. 9, 2016, 2016/0289392, Oct. 6, 2016.

U.S. Appl. No. 15/065,317, filed Mar. 9, 2016, 2017/0018801, Jan. 19, 2017.

U.S. Appl. No. 15/228,876, filed Aug. 4, 2016, 2017/0062874, Mar. 2, 2017.

U.S. Appl. No. 15/243,788, filed Aug. 22, 2016, 2016/0356923, Dec. 8, 2016.

* cited by examiner

ORGANIC SYNTHESIS APPLICATIONS OF NON-AQUEOUS FLUORIDE SALT SOLUTIONS

CROSS-REFERENCE TO RELATED APPLICATION(S)

This application claims the benefit of and priority to U.S. Provisional Application No. 62/200,998, filed on Aug. 4, 2015, and entitled "Non-Aqueous Fluoride Salts, Solutions and their uses," the entire teachings of which are incorporated herein by reference.

GOVERNMENT SUPPORT

The invention described herein was made in the performance of work under a NASA contract NNN12AA01C, and is subject to the provisions of Public Law 96-517 (35 USC 202) in which the Contractor has elected to retain title.

BACKGROUND

Solutions containing fluoride ions ($F^-$) are useful in a range of chemical applications. However, aqueous solutions containing $F^-$ are problematic. For example, $F^-$ reacts rapidly with water, forming hydrogen fluoride (HF) and the complex ion $HF_2^-$. HF is generally undesirable due to its highly toxic and corrosive nature. Furthermore, $HF_2^-$ is much less active, or even inactive, than $F^-$ in applications such as synthesis and electrochemistry.

To avoid these problems, the use of non-aqueous $F^-$ solutions is desirable. Notably, though, non-aqueous solutions of $F^-$ have proven difficult to prepare in concentrations high enough to be useful (e.g., greater than or equal to 0.05 M). For example, metal fluorides are highly insoluble in non-aqueous solvents, even in the presence of "solubilizing" species, such as crown ethers. Organic fluorides are typically difficult to dry to remove water contamination due to reactivity of the organic cation with $F^-$ under the drying conditions. Furthermore, in certain cases where anhydrous organic fluoride compounds are known, these compounds are poorly soluble in non-aqueous solvents.

Accordingly, there exists an ongoing need for $F^-$ solutions having improved $F^-$ concentration.

SUMMARY

Embodiments of the disclosure provide processes and reaction mixtures including non-aqueous solvent mixtures. Non-aqueous solvent mixtures including fluoride salt and non-aqueous solvent combinations, for example, are provided that possess high fluoride ion concentrations that are useful for a range of applications, including organic synthesis and catalysis. Non-aqueous solvent mixtures including combinations of one or more salts possessing a non-fluoride anion and one or more non-aqueous solvents are further provided that, when contacted with aqueous fluoride-containing reagents, are useful for extraction of fluoride ions to form non-aqueous fluoride ion-containing solutions possessing high fluoride-ion concentrations.

In some embodiments, the molecular structure of the salt cations within these non-aqueous solvent mixtures facilitates their ability to (i) be made in anhydrous form without substantial decomposition and (ii) to achieve efficient dissociation to generate high fluoride ion concentrations in non-aqueous solvents. For example, the salts include an organic cation (e.g., with N, P, S, or O charge center) that does not possess a carbon in the β-position or does not possess a carbon in the β-position having a bound hydrogen. In certain embodiments, the organic cation does not possess an $sp^3$-hybridized carbon in the β-position having a bound hydrogen.

Examples of organic cations may include, but are not limited to, alkyl ammonium cations. Such alkylammonium cations may include, but are not limited to, (2,2-dimethylpropyl)trimethylammonium ($NpMe_3N^+$), Bis(2,2-dimethylpropyl)dimethylammonium ($Np_2Me_2N^+$), and Tris(2,2-dimethylpropyl)methylammonium ($Np_3MeN^+$). Embodiments of suitable fluoride salts may include any of these cations with a fluoride anion (e.g., $NpMe_3NF$, $Np_2Me_2NF$, $Np_3MeNF$). Embodiments of suitable salts having a non-fluoride anion may include any of these cations with an easily exchangeable, non-fluoride anion that is soluble in non-aqueous solvents. Examples of such anions may include, but are not limited to, hydroxide, alkoxide, iodide, acetate, carbonate, bicarbonate, sulfonate, arenesulfonate, alkylsulfonate, triflate, bis(trifluoromethylsulfonyl)imide (TFSI), and trifluoroacetate, and at least partially fluorinated or substituted analogs thereof.

Embodiments of the disclosure provide non-aqueous solutions of the fluoride salts characterized by high fluoride-ion concentrations in one or more non-aqueous solvents (e.g., greater than or equal to 0.05 M and, in certain cases, up to 20 M). As discussed in greater detail below, it has been identified that the combination of these fluoride salts with at least one fluorine-containing, non-aqueous solvent promotes dissociation and solubility of the fluoride salts within the non-aqueous solvents. Without being bound by theory, for example, it is believed that solvents having structures including $CH_2$ moieties adjacent to electron-withdrawing groups (e.g., O and/or $CF_3$) give rise to increased partial positive charge on the $CH_2$ moieties. The partial positive charge on the $CH_2$ moieties further promotes fluoride ion and cation solvation and attendant solubility of the fluoride salts.

For example, as discussed in greater detail below, theoretical calculations comparing the solvation free energies of fluoride ions and different cations in solvents with and without $CH_2$ moieties (e.g., characterized by the form $X—CH_2—Y—CH_2—X$ or $X—(CH_2)_2—Y—(CH_2)_2—X$, where X, Y are electron-withdrawing groups), illustrates that solvents lacking $CH_2$ moieties exhibit a pronounced decrease in fluoride solubility. Furthermore, solvents having structures including $CH_2$ moieties adjacent to electron withdrawing groups exhibit up to a ten-fold increase in the calculated fluoride solvation free energy, as compared to solvents structures lacking $CH_2$ moieties adjacent to electron withdrawing groups. Additionally, the presence of electron density modifying groups, such as electron donating and/or electron withdrawing groups adjacent the cation charge center, may modify the attraction of the cation to the solvent, allowing the cation to be tuned to different solvents for enhanced solubility.

Non-aqueous solutions of the disclosed embodiments are compatible with a range of fluorinated and non-fluorinated solvents. Examples of the fluorinated, non-aqueous solvents may include, but are not limited to, bis(2,2,2-trifluoroethyl) ether (BTFE). In further embodiments, the solvent may be a mixture of at least one non-aqueous fluorine-containing solvent (e.g., BTFE) and at least one non-aqueous, non-fluorine containing solvent (e.g., propionitrile (PN) or dimethoxyethane (DME)). For example, as discussed in detail below, $F^-$-containing solutions including solvent mixtures of BTFE/PN are observed to exhibit higher conductivity than pure BTFE at the same molarity. Without being bound by theory, it is believed that solvents such as BTFE can charge separate and/or dissolve the fluoride salt in high concentration as ion pairs, whereas solvents such as PN dissociate the $F^-$ salt but is not polar enough itself to dissolve the salt in comparable concentrations in pure solvent.

Additional embodiments of the disclosure present use of these high concentration $F^-$ solutions in organic synthesis applications, such as substitution, elimination, addition, coupling, deprotection and catalysis, as well as radiolabeling.

In an embodiment, a first process for chemical synthesis is provided. The process includes contacting one or more reagents with a non-aqueous solvent mixture. The non-aqueous solvent mixture includes a fluoride salt and one or more non-aqueous solvent. The fluoride salt includes one or more fluoride ions and an organic cation. The organic cation does not possess a carbon in the β-position or does not possess a carbon in the β-position having a bound hydrogen, where the cation charge center is N, P, S, or O. A concentration of the fluoride ions dissolved in the non-aqueous solvent mixture is greater than or equal to 0.05 M.

In an embodiment, a second process for solvent extraction is provided. The process includes contacting an aqueous fluoride ion-containing reagent with a non-aqueous solvent mixture. The non-aqueous solvent mixture includes one or more non-aqueous solvents and a salt. The salt includes a non-fluoride anion soluble in the non-aqueous solvent and an organic cation that does not possess a carbon in the β-position or does not possess a carbon in the β-position having a bound hydrogen, where the cation charge center is N, P, S, or O. At least a portion the fluoride ions are extracted from the aqueous reagent to the non-aqueous solvent mixture.

Embodiments of either or both of the first and second processes may include one or more of the following, in any combination.

In an embodiment, the contacting step results in a fluorine-containing reaction product, a fluorine-involving reaction intermediate, or a fluorine-involving catalytic process.

In an embodiment, the salt is provided to the non-aqueous solvent in an anhydrous form.

In an embodiment, the fluoride ions include a radioactive fluorine isotope.

In an embodiment, a concentration of fluoride anions dissolved in the non-aqueous solvent mixture is selected over the range of 0.05 M to 20 M.

In an embodiment, a concentration of fluoride anions dissolved in the non-aqueous solvent mixture after the contacting is selected over the range of 0.05 M to 20 M.

In an embodiment, a concentration of fluoride ions is greater than or equal to 1 M.

In an embodiment, the reagent is $H^{18}F$ in water or $H^{19}F$ in water.

In an embodiment, the organic cation is selected from the group consisting of: (2,2-dimethylpropyl)trimethylammonium ($NpMe_3N^+$), bis(2,2-dimethylpropyl)dimethylammonium ($Np_2Me_2N^+$), and tris(2,2-dimethylpropyl)methylammonium ($Np_3MeN^+$).

In an embodiment, the non-fluoride anion is selected from the group consisting of: hydroxide, alkoxide, iodide, acetate, carbonate, bicarbonate, sulfonate, arenesulfonate, alkylsulfonate, bis(trifluoromethylsulfonyl)imide (TFSI), triflate, trifluoroacetate, and at least partially fluorinated or substituted analogs thereof.

In an embodiment, the contacting step produces an $^{18}F^-$ or $^{19}F^-$ salt selected from the group consisting of $NpMe_3NF$, $Np_2Me_2NF$, and $Np_3MeNF$ dissolved in the non-aqueous solution.

In an embodiment, the contacting step produces a first reaction product by a reaction mechanism selected from the group consisting of substitution, addition, elimination, reaction as a base, deprotection, and fluorination involving the fluoride ions.

In an embodiment, the reagent includes an organic compound including an anion and where the contacting step produces a first reaction product by nucleophilic substitution of the fluoride ions for the anion of said organic compound.

In an embodiment, the contacting step further produces a second reaction product by elimination of the anion of said organic compound.

In an embodiment, an amount of the first reaction product exceeds an amount of the second reaction product.

In an embodiment, a concentration of fluoride anions dissolved in the non-aqueous solvent mixture is at least 1M.

In an embodiment, the organic cation does not possess a carbon in the β position or does not possess an $sp^3$-hybridized carbon in the β-position having a bound hydrogen.

In an embodiment, the organic cation includes a substituted or unsubstituted alkylammonium cation characterized by the formula (FX1): $R^1R^2R^3R^4N^+$ (FX1), where each of $R^1$, $R^2$, $R^3$, and $R^4$ is independently a substituted or unsubstituted $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_{20}$ alkyl, $C_2$-$C_{20}$ alkoxycarbonyl, or halo, or where at least two of $R^1$-$R^4$ combine to form one or more alicyclic or aromatic, carbocyclic or heterocyclic 5 or 6 membered rings.

In an embodiment, at least one of $R^1$, $R^2$, $R^3$, and $R^4$ is independently a halogen substituted substituent.

In an embodiment, at least one of $R^1$, $R^2$, $R^3$, and $R^4$ is independently a fluorine substituted substituent.

In an embodiment, at least one of $R^1$, $R^2$, $R^3$, and $R^4$ independently is a polar substituent.

In an embodiment, at least one of $R^1$, $R^2$, $R^3$, and $R^4$ is independently a polar group selected from the group consisting of substituted or unsubstituted phenyl, benzyl, or heterocyclic species.

In an embodiment, the organic cation is characterized by the formula (FX2a), (FX2b), (FX2c), or (FX2d):

(FX2a)

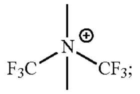

(FX2b)

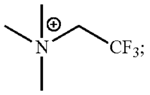

(FX2c)

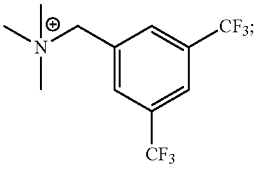

or

-continued (FX2d)

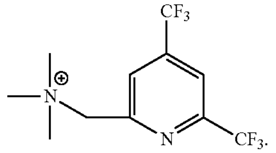

In an embodiment, the organic cation is a substituted or unsubstituted neo-pentyl ammonium cation.

In an embodiment, the substituted or unsubstituted neo-pentyl ammonium cation is characterized by the formula (FX3a), (FX3b), (FX3c), or (FX3d):

(FX3a)

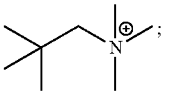

(FX3b)

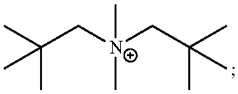

(FX3c)

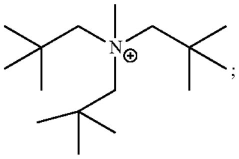

or (FX3d)

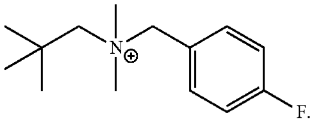

In an embodiment, the ammonium cation includes a substituted or unsubstituted benzylammonium cation.

In an embodiment, the substituted or unsubstituted benzylammonium cation is characterized by the formula (FX4a) or (FX4b):

(FX4a)

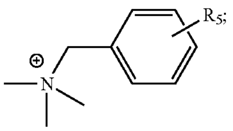

or (FX4b)

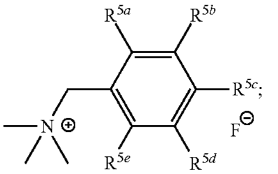

where $R^5$ is O—$R^6$, N—$R^6$, $CO_2$—$R^6$ $CF_3$, $SF_5$, or —$SO_2R^6$; $R^{5a}$—$R^{5e}$ are independently selected from H, O—$R^6$, N—$R^6$, $CO_2$—$R^6$, $CF_3$, $SF_5$, or —$SO_2R^6$, and $R^6$ is H, $C_1$-$C_{10}$ alkyl, or $C_1$-$C_{10}$ aryl.

In an embodiment, $R^5$ is one of N—$(CH_3)_2$, O—$CH_3$, $CO_2$—$CH_3$ or $CF_3$.

In an embodiment, the organic cation includes a substituted or unsubstituted hexamethylenetetramine (HMT) cation.

In an embodiment, the HMT cation is characterized by the formula (FX5a), (FX5b), (FX5c), or (FX5d):

(FX5a)

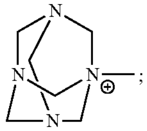

(FX5b)

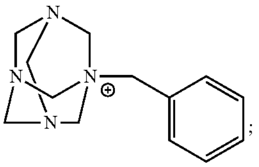

(FX6c)

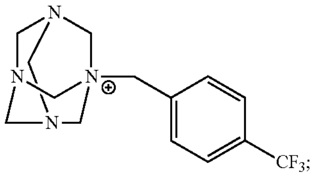

or (FX5d)

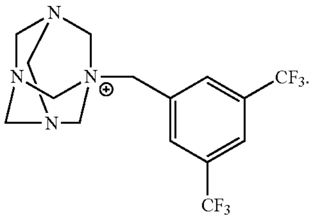

In an embodiment, the organic cation is a substituted or unsubstituted, saturated or unsaturated heterocyclic cation and where the heterocyclic cation includes one or more nitrogen, oxygen, sulfur, or phosphorus atoms as part of a four-, five-, six-, or seven-membered ring; one or more of the heterocyclic cations bears a formal charge conferred through alkylation of the heterocyclic cation; and the heterocyclic cation does not possess a carbon in the β-position or does not possess an $sp^3$-hybridized carbon in the β-position having a bound hydrogen.

In an embodiment, the heterocyclic cation is characterized by the formula (FX6a), (FX6b), (FX6c), (FX6d), (FX6e), (FX6f), (FX6g), (FX6h), or (FX6i):

(FX6a)

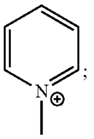

(FX6b)

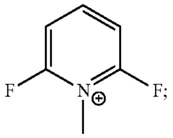

-continued (FX6c)

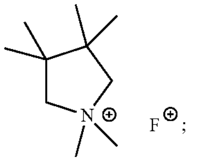

(FX6d)

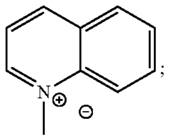

(FX6e)

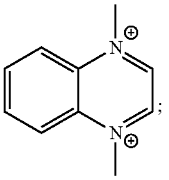

(FX6f)

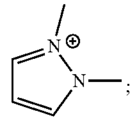

(FX6g)

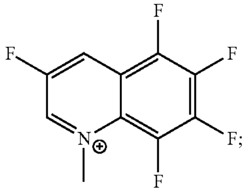

(FX6h)

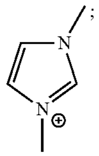

or (FX6i)

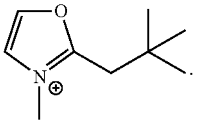

In an embodiment, the non-aqueous solvent is one or more fluorinated non-aqueous solvent.

In an embodiment, the non-aqueous solvent includes at least one functional group characterized by the form [X—$(CH_2)_n$—Y], where X and Y are polar functional groups having a combined effect to confer a partial positive charge on the $CH_2$ group or groups and n=1 or 2.

In an embodiment, Y is O or S and X is a functional group selected from the group consisting of ethers, esters, acid anhydrides, amines, amides, carbonates, sulfones, sulfonyl esters, phosphites, phosphates, nitriles, nitro, aldehydes, acetates, $SF_5$, or fluorocarbons.

In an embodiment, the non-aqueous solvent is an aromatic solvent including at least one functional group characterized by the form [X—$(CH_2)_n$—Y], where n=1 or 2.

In an embodiment, the non-aqueous solvent is a fluorinated ether and any combination thereof.

In an embodiment, the fluorinated ether is characterized by the formula (FX7a), (FX7b), (FX7c), (FX7d), (FX7e), (FX7f), or (FX7g):

(FX7a)

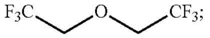

(FX7b)

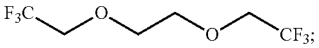

(FX7c)

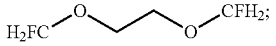

(FX7d)

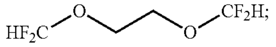

(FX7e)

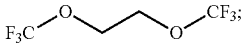

(FX7f)

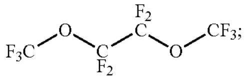

or (FX7g)

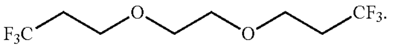

In an embodiment, the non-aqueous solvent is a fluorinated phosphite and any combination thereof.

In an embodiment, the fluorinated phosphite is characterized by the formula (FX8a):

(FX8a)

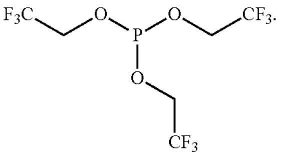

In an embodiment, the non-aqueous solvent is a fluorinated ester or anhydride and any combination thereof.

In an embodiment, the fluorinated ester or anhydride is characterized by the formula (FX9a), (FX9b), or (FX9c):

(FX9a)

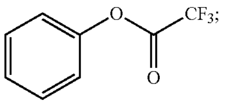

(FX9b)

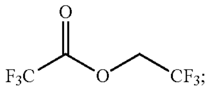

or (FX9c)

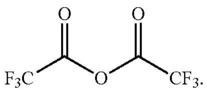

In an embodiment, the non-aqueous solvent is a nitrile and any combination thereof.

In an embodiment, the nitrile is characterized by the formula (FX10a), (FX10b), (FX10c), or (FX10d):

(FX10a)

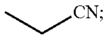

(FX10b)

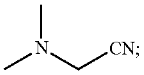

(FX10c)

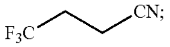 or (FX10d)

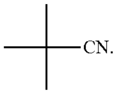

In an embodiment, the non-aqueous solvent is a fluorine-substituted aromatic solvent and any combination thereof.

In an embodiment, the fluorine-substituted aromatic is characterized by the formula (FX11a), (FX11b), (FX11c), or (FX11d):

(FX11a)

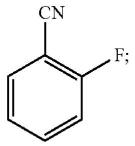

(FX11b)

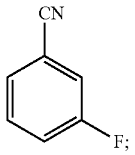

(FX11c)

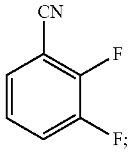 or (FX11d)

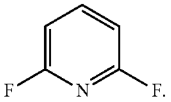

In an embodiment, the non-aqueous solvent is characterized by the formula (FX12a) or (FX12b) and any combination thereof:

(FX12a)

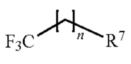 or (FX12b)

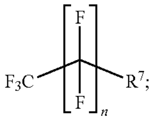

where $R^7$ is a substituted or unsubstituted $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_{20}$ alkyl, $C_2$-$C_{20}$ alkoxycarbonyl, halo, $C_4$-$C_{30}$ aliphatic, $C_4$-$C_{30}$ cycloaliphatic, or $C_4$-$C_{30}$ aromatic; and where n is an integer selected from the range of 1 to 20.

In an embodiment, a first reaction mixture is provided. The first reaction mixture includes one or more reagents; and a non-aqueous solvent mixture. The non-aqueous solvent mixture includes a fluoride salt and one or more non-aqueous solvent. The fluoride salt includes one or more fluoride ions; and an organic cation that does not possess a carbon in the β-position or does not possess a carbon in the β-position having a bound hydrogen, where the cation charge center is N, P, S, or O. A concentration of the fluoride ions dissolved in the non-aqueous solvent mixture is greater than or equal to 0.05 M.

In an embodiment, a second reaction mixture is provided. The second reaction mixture includes an aqueous fluoride ion-containing reagent and a non-aqueous solvent mixture. The non-aqueous solvent mixture includes one or more non-aqueous solvents and a salt. The salt includes a non-fluoride anion soluble in the non-aqueous solvent and an organic cation that does not possess a carbon in the β-position or does not possess a carbon in the β-position having a bound hydrogen, where the cation charge center is N, P, S, or O. At least a portion the fluoride ions are extracted from the aqueous reagent to the non-aqueous solvent mixture.

Embodiments of either or both of the first and second reaction mixtures may include one or more of the following, in any combination.

In an embodiment, the contacting step results in a fluorine-involving reaction intermediate, or a fluorine-involving catalytic process.

In an embodiment, the salt is provided to the non-aqueous solvent in an anhydrous form.

In an embodiment, the fluoride ions include a radioactive fluorine isotope.

In an embodiment, a concentration of fluoride anions dissolved in the non-aqueous solvent mixture is selected over the range of 0.05 M to 20 M.

In an embodiment, a concentration of fluoride anions dissolved in the non-aqueous solvent mixture after the contacting is selected over the range of 0.05 M to 20 M.

In an embodiment, the concentration of fluoride ions is greater than or equal to 1 M.

In an embodiment, the reagent is $H^{18}F$ in water or $H^{19}F$ in water.

In an embodiment, the cation of the salt precursor is selected from the group consisting of: (2,2-dimethylpropyl) trimethylammonium ($NpMe_3N^+$), bis(2,2-dimethylpropyl) dimethylammonium ($Np_2Me_2N^+$), and tris(2,2-dimethylpropyl)methylammonium ($Np_3MeN^+$).

In an embodiment, the non-fluoride anion is selected from the group consisting of: hydroxide, alkoxide, iodide, acetate, carbonate, bicarbonate, sulfonate, arenesulfonate, alkylsulfonate, bis(trifluoromethylsulfonyl)imide (TFSI), triflate, trifluoroacetate, and at least partially fluorinated or substituted analogs thereof.

In an embodiment, the reaction mixture produces an $^{18}F^-$ or $^{19}F^-$ salt selected from the group consisting of $NpMe_3NF$, $Np_2Me_2NF$, and $Np_3MeNF$ dissolved in the non-aqueous solution.

In an embodiment, the reaction mixture produces a first reaction product by a reaction mechanism selected from the group consisting of substitution, addition, elimination, reaction as a base, deprotection, and fluorination involving the fluoride ions.

In an embodiment, the reagent includes an organic compound including an anion and further producing a first reaction product by nucleophilic substitution of the fluoride ions for the anion of said organic compound from contact of the reagent and the non-aqueous solvent mixture.

In an embodiment, the reaction mixture produces a second reaction product by elimination of the anion of said organic compound from contact of the reagent and the non-aqueous solvent mixture.

In an embodiment, an amount of the first reaction product formed exceeds an amount of the second reaction product.

In an embodiment, a concentration of fluoride anions dissolved in the non-aqueous solvent mixture is at least 1M.

In an embodiment, the organic cation does not possess a carbon in the β position or does not possess an $sp^3$-hybridized carbon in the β position having a bound hydrogen.

In an embodiment, the organic cation includes a substituted or unsubstituted alkylammonium cation characterized by the formula (FX1): $R^1R^2R^3R^4N^+$ (FX1); where each of $R^1$, $R^2$, $R^3$, and $R^4$ is independently a substituted or unsubstituted $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_{20}$ alkyl, $C_2$-$C_{20}$ alkoxycarbonyl, or halo; or where at least two of $R^1$-$R^4$ combine to form one or more alicyclic or aromatic, carbocyclic or heterocyclic 5 or 6 membered rings.

In an embodiment, at least one of $R^1$, $R^2$, $R^3$, and $R^4$ is independently a halogen substituted substituent.

In an embodiment, at least one of $R^1$, $R^2$, $R^3$, and $R^4$ is independently a fluorine substituted substituent.

In an embodiment, at least one of $R^1$, $R^2$, $R^3$, and $R^4$ independently is a polar substituent.

In an embodiment, at least one of $R^1$, $R^2$, $R^3$, and $R^4$ is independently a polar group selected from the group consisting of substituted or unsubstituted phenyl, benzyl, or heterocyclic species.

In an embodiment, the organic cation is characterized by the formula (FX2a), (FX2b), (FX2c), or (FX2d):

(FX2a)

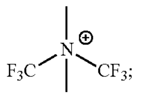

(FX2b)

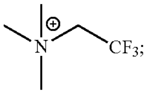

(FX2c)

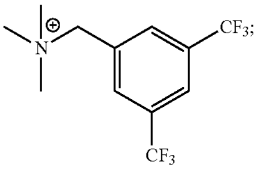

or (FX2d)

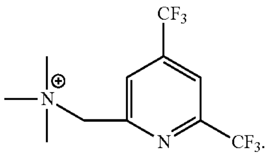

In an embodiment, the organic cation is a substituted or unsubstituted neo-pentyl ammonium cation.

In an embodiment, the substituted or unsubstituted neopentyl ammonium cation is characterized by the formula (FX3a), (FX3b), (FX3c), or (FX3d):

(FX3a)

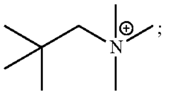

(FX3b)

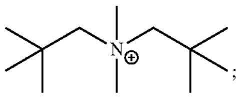

(FX3c)

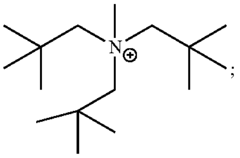

or (FX3d)

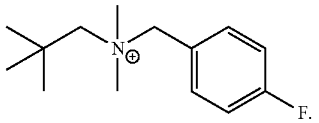

In an embodiment, the organic cation includes a substituted or unsubstituted benzylammonium cation.

In an embodiment, the substituted or unsubstituted benzylammonium cation is characterized by the formula (FX4a) or (FX4b):

(FX4a)

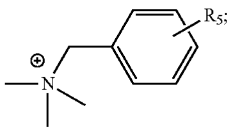

or (FX4b)

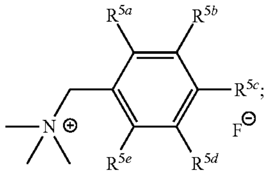

where $R^5$ is O—$R^6$, N—$R^6$, $CO_2$—$R^6$ $CF_3$, $SF_5$, or —$SO_2R^6$, $R^{5a}$—$R^{5e}$ are independently selected from H, O—$R^6$, N—$R^6$, $CO_2$—$R^6$, $CF_3$, $SF_5$, or —$SO_2R^6$, and $R^6$ is H, $C_1$-$C_{10}$ alkyl, or $C_1$-$C_{10}$ aryl.

In an embodiment, $R^5$ is one of N—$(CH_3)_2$, O—$CH_3$, $CO_2$—$CH_3$ or $CF_3$.

In an embodiment, the organic cation includes a substituted or unsubstituted hexamethylenetetramine (HMT) cation.

In an embodiment, the HMT cation is characterized by the formula (FX5a), (FX5b), (FX5c), or (FX5d):

(FX5a)

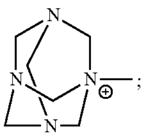

-continued (FX5b)

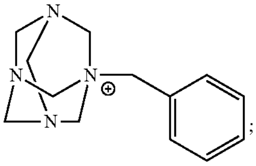

(FX6c)

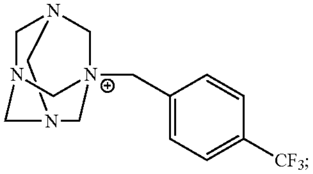

or (FX5d)

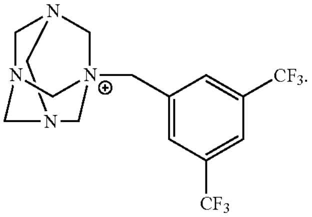

In an embodiment, the organic cation is a substituted or unsubstituted, saturated or unsaturated heterocyclic cation and where the heterocyclic cation includes one or more nitrogen, oxygen, sulfur, or phosphorus atoms as part of a four-, five-, six-, or seven-membered ring; one or more of the heterocyclic cations bears a formal charge conferred through alkylation of the heterocyclic cation; and the heterocyclic cation does not possess a carbon in the β-position or does not possess an $sp^3$-hybridized carbon in the β-position having a bound hydrogen.

In an embodiment, the heterocyclic cation is characterized by the formula (FX6a), (FX6b), (FX6c), (FX6d), (FX6e), (FX6f), (FX6g), (FX6h), or (FX6i):

(FX6a)

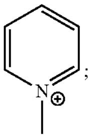

(FX6b)

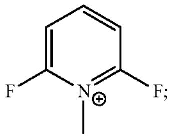

(FX6c)

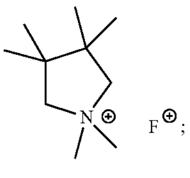

(FX6d)

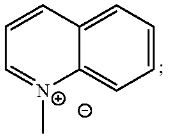

-continued (FX6e)

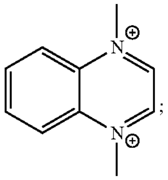

(FX6f)

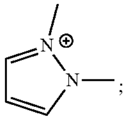

(FX6g)

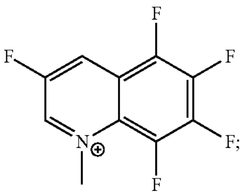

(FX6h)

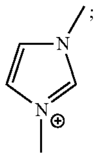

or (FX6i)

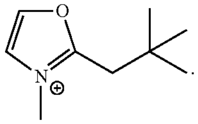

In an embodiment, the non-aqueous solvent is one or more fluorinated non-aqueous solvent.

In an embodiment, the non-aqueous solvent includes at least one functional group characterized by the form [X—$(CH_2)_n$—Y—], where X and Y are polar functional groups having a combined effect to confer a partial positive charge on the $CH_2$ group or groups and n=1 or 2.

In an embodiment, Y is O or S and X is a functional group selected from the group consisting of ethers, esters, acid anhydrides, amines, amides, carbonates, sulfones, sulfonyl esters, phosphites, phosphates, nitriles, nitro, aldehydes, acetates, $SF_5$, or fluorocarbons.

In an embodiment, the non-aqueous solvent is an aromatic solvent including at least one functional group characterized by the form [X—$(CH_2)_n$—Y], where n=1 or 2

In an embodiment, the non-aqueous solvent is a fluorinated ether and any combination thereof.

In an embodiment, the fluorinated ether is characterized by the formula (FX7a) or (FX7b), (FX7c), (FX7d), (FX7e), (FX7f), or (FX7g):

(FX7a)

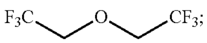

(FX7b)

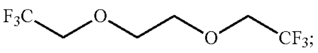

(FX7c)

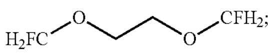

-continued (FX7d)

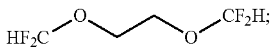

(FX7e)

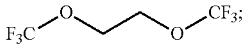

(FX7f)

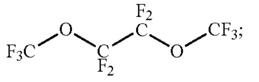

or (FX7g)

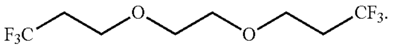

In an embodiment, the non-aqueous solvent is a fluorinated phosphite and any combination thereof.

In an embodiment, the fluorinated phosphite is characterized by the formula (FX8a):

(FX8a)

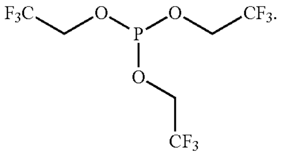

In an embodiment, the non-aqueous solvent is a fluorinated ester or anhydride and any combination thereof.

In an embodiment, the fluorinated ester or anhydride is characterized by the formula (FX9a), (FX9b), or (FX9c):

(FX9a)

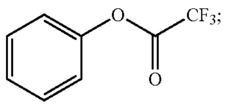

(FX9b)

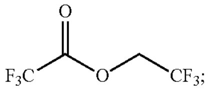

or (FX9c)

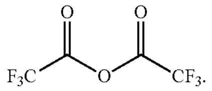

In an embodiment, the non-aqueous solvent is a nitrile and any combination thereof.

In an embodiment, the nitrile is characterized by the formula (FX10a), (FX10b), (FX10c), or (FX10d):

(FX10a)

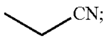

(FX10b)

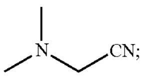

(FX10c)

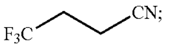

or

-continued (FX10d)

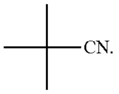

In an embodiment, the non-aqueous solvent is a fluorine-substituted aromatic solvent and any combination thereof.

In an embodiment, the fluorine-substituted aromatic is characterized by the formula (FX11a), (FX11b), (FX11c), or (FX11d):

(FX11a)

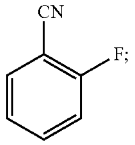

(FX11b)

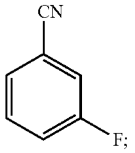

(FX11c)

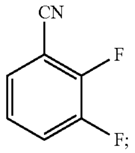

or (FX11d)

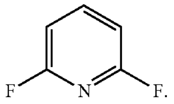

In an embodiment, the non-aqueous solvent is characterized by the formula (FX12a) or (FX12b) and any combination thereof:

(FX12a)

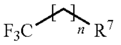

or (FX12b)

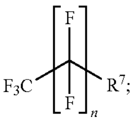

where $R^7$ is a substituted or unsubstituted $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_{20}$ alkyl, $C_2$-$C_{20}$ alkoxycarbonyl, halo, $C_4$-$C_{30}$ aliphatic, $C_4$-$C_{30}$ cycloaliphatic, or $C_4$-$C_{30}$ aromatic; and where n is an integer selected from the range of 1 to 20.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of the disclosed embodiments.

"Carbon in the β-position" or "β-carbon" refers to a carbon atom one removed from an atom, group, functional group, or other moiety of interest. In certain embodiments, the functional group of interest is a quaternary alkylammonium functional group and the β-carbon is the second carbon from the alkylammonium functional group.

"Anhydrous" refers to compositions, including salts such as fluoride salts, that are substantially free of water. In an embodiment, for example, anhydrous fluoride salts are provided that are characterized by an amount of water less than 1000 parts per million (ppm) and in some embodiments less than 100 parts per million (ppm).

Figure 1:
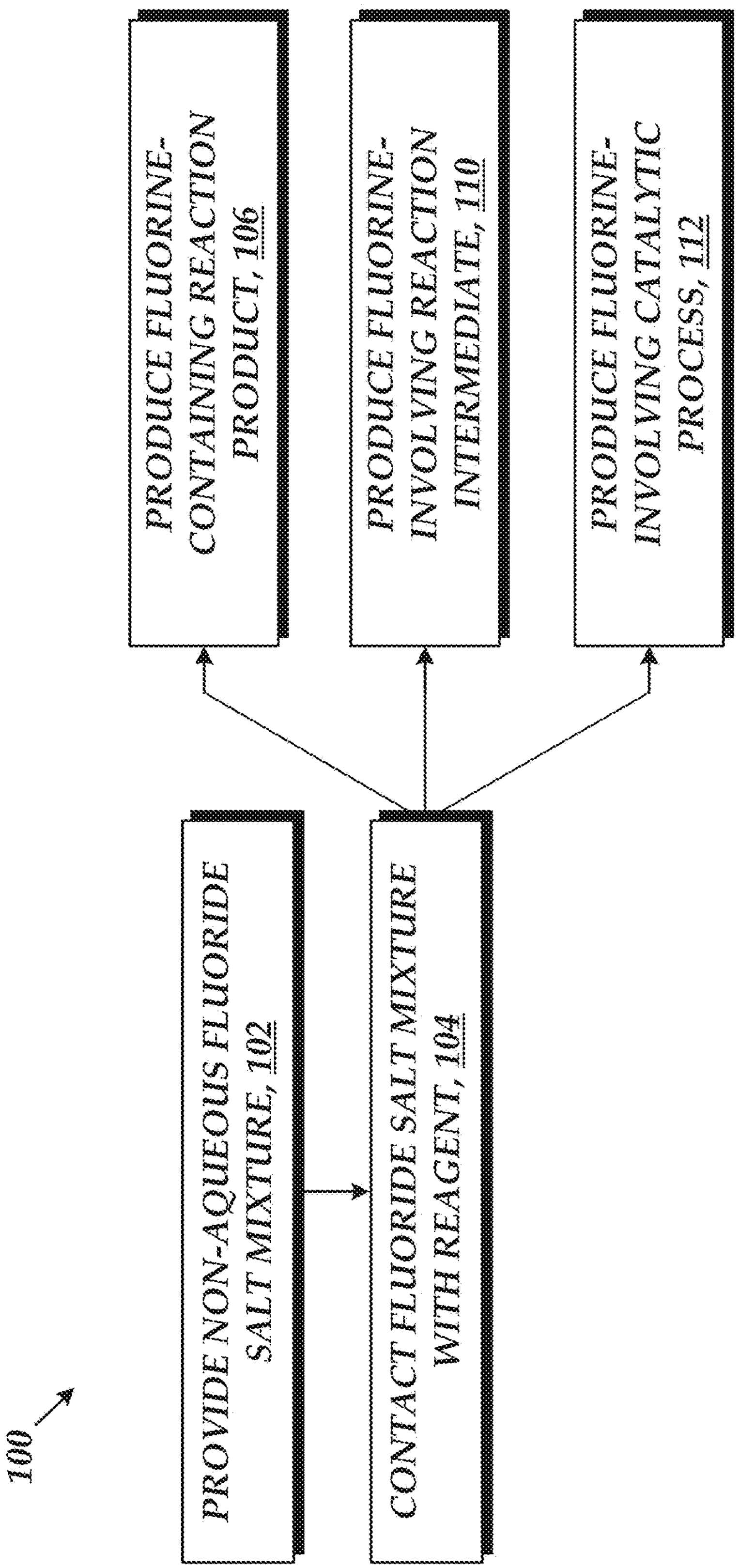
FIG. 1 is a schematic flow diagram illustrating an embodiment of a process for organic synthesis employing non-aqueous fluoride ion-containing solutions of the present disclosure.

Processes and Reaction Mixtures Including Non-Aqueous Fluoride-Ion Solutions for Chemical Synthesis With reference to FIG. 1, an embodiment of a process 100 for chemical synthesis employing fluoride-ion containing solutions is provided. The process 100 includes providing a non-aqueous solvent mixture in step 102 and contacting one or more reagents with the non-aqueous solvent mixture in step 104. The non-aqueous solvent mixture includes a fluoride salt, where the fluoride salt is designed such that a concentration of the fluoride ions dissolved in the fluoride ion solvent mixture is greater than or equal to 0.05 M. The high concentration of fluoride ions dissolved in solution, when contacting the one or more reagents, results in at least one fluorine-containing reaction product (step 106), at least one fluorine-involving reaction intermediate (110), and/or a fluorine-involving catalytic process (step 112). In particular, such high fluoride ion concentrations may provide control over product distribution and/or high rates of reaction. Representative chemical synthesis are discussed in greater detail below in the Examples. It may be understood that, in alternative embodiments, the process 100 may include greater or few steps and that the steps may be performed in a different order than that illustrated in FIG. 1.

Fluoride salts, non-aqueous solvents, and solvent mixtures suitable for use in embodiments of the process 100 are discussed in detail below.

Anhydrous Fluoride Salts

Design considerations of embodiments of the fluoride salts are discussed below. In some embodiments, the fluoride salts are provided to the non-aqueous solvent in an anhydrous state to form the non-aqueous solvent mixture. As further discussed below in the Examples, solutions containing embodiments of the anhydrous fluoride salts and one or more non-aqueous solvents exhibit a concentration of fluoride ions dissolved within one or more non-aqueous solvents that is greater than or equal to 0.05 M. In further embodiments, the concentration of fluoride ions dissolved within one or more non-aqueous solvents is up to 20 M. In additional embodiments, the concentration of fluoride ions is selected over the range of 0.05 M to 20 M.

Figure 3:
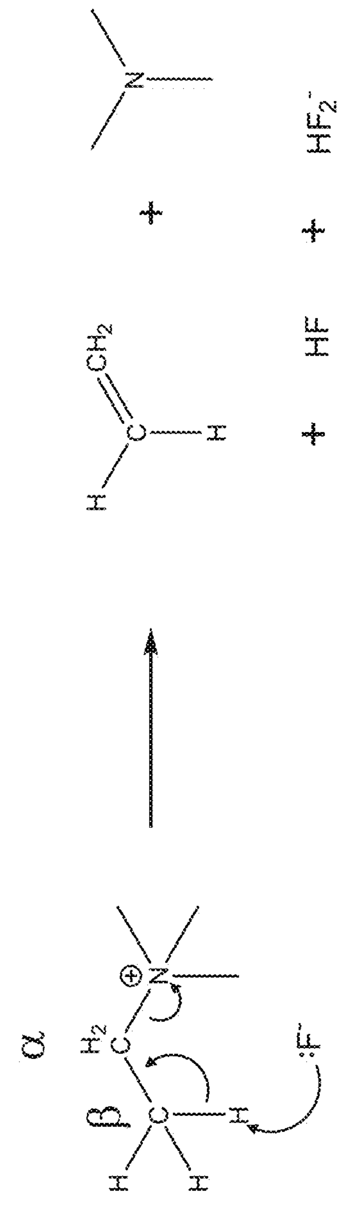
FIG. 3 is an illustration of decomposition of a tetraalkylammonium fluoride salt under drying conditions to form HF and $HF_2^-$.

Anhydrous fluoride salts are desirable as, in water, the fluoride ion reacts with the water to form HF and $HF_2^-$. However, anhydrous fluoride salts are difficult to manufacture. For example, with reference to a quaternary alkylammonium fluoride salt in FIG. 3, under drying conditions, the fluoride ion reacts with hydrogen bound to the β-carbon of the quaternary alkylammonium functional group (N—$(CH_3)_3$)–$^+$ (i.e., two carbon atoms removed from the nitrogen charge center) and will eliminate to form HF and $HF_2^-$.

In one embodiment, formation of fluoride salts in the anhydrous state, while avoiding production of HF and/or $HF_2^-$ during drying, may be achieved by using fluoride salts including one or more fluoride ions and an organic cation, where the organic cation does not possess a carbon in the β-position having a bound hydrogen, as this bound hydrogen will react upon drying. In another embodiment, this goal may be achieved by fluoride salts including one or more fluoride ions and an organic cation, where the organic cation does not possess a carbon in the β-position. In either case, the cation charge center may be selected from nitrogen (N), phosphorus (P), sulfur (S), or oxygen (O).

Notably, it has been observed that the absence of a carbon in the β-position, or the absence of a carbon in the β-position having a bound hydrogen, may not be sufficient to promote high levels of solubility of the fluoride salt with non-aqueous solvents. For example, consider tetramethylammonium fluoride (TMAF):

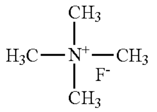

tetramethylammonium fluoride (TMAF)

As discussed in detail below, it has been observed that TMAF is not very soluble in non-aqueous solvents.

It has been identified that solubility of fluoride salts that do not contain a carbon in the β-position, or do not possess a carbon in the β-position having a bound hydrogen, may be improved by increasing the degree of alkylation and/or substitution of the cation and/or decreasing the symmetry of the cation. For example, one solution is to substitute the cation with neo-pentyl (2,2-dimethylpropyl) groups, as illustrated in Table 1, therefore avoiding Hofmann elimination upon drying, while increasing solubility through alkylation.

TABLE 1

Substitution of TMAF with neo-pentyl (2,2-dimethylpropyl) groups

| Cation | Hofmann elimination | # of hydrogens bound to β-carbon |
|---|---|---|
| 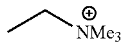 | Yes | 3 |
| 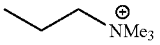 | Yes | 2 |
| 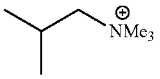 | Yes | 1 |
| 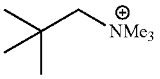 | No | 0 |

As discussed below, neo-pentyl fluoride salts may include, but are not limited to, (2,2-dimethylpropyl)trimethylammonium fluoride ($NpMe_3NF$) and bis(2,2-dimethylpropyl)dimethylammonium fluoride ($Np_2Me_2NF$). In general, embodiments of the anhydrous fluoride salt may be substituted or unsubstituted ammonium fluoride salts.

Without being bound by theory, it is believed that alkylation and/or substitution of the alkylammonium cation with electron-donating or electron-withdrawing modifies the charge on the cation charge center. Furthermore, as discussed in greater detail below with regards to the solvent and the Examples, when solvents including $CH_2$ moieties having a partial positive charge are combined with such salts, solvation of the cation, as well as the fluoride anions, by the solvent may be improved.

Non-Aqueous Solvents

Solvent screening performed using $NpMe_3NF$ as the salt are discussed in detail below in Example 3. Suitable non-aqueous solvent embodiments identified from this screening are outlined below. In an embodiment, the non-aqueous solvent includes at least one fluorinated, non-aqueous solvent. In an embodiment, the non-aqueous solvent is characterized by the form $XCH_2YCH_2X$ or $XCH_2CH_2YCH_2CH_2X$ (i.e., $[X—(CH_2)_n—Y]$, where n=1 or 2), where X and Y are polar functional groups (i.e., electron withdrawing groups) having a combined effect to confer a partial positive charge on the $CH_2$ group or groups.

For example, Y may be O or S. X may be a functional group including, but not limited to, ethers, esters, acid anhydrides, amines, amides, carbonates, sulfones, sulfonyl esters, phosphites, phosphates, nitriles, nitro, aldehydes, acetates, $SF_5$, or fluorocarbons (e.g., $—CF_3$, $—CF_2CF_3$).

In another embodiment, the non-aqueous solvent is an aromatic solvent including at least one functional group characterized by the form $[X—(CH_2)_n—Y]$, where n=1 or 2 and where X and Y are polar functional groups having a combined effect to confer a partial positive charge on the $CH_2$ group or groups. In another embodiment of the electrolyte solution, Y is O or S and X is a functional group selected from the group including, but not limited to, ethers, esters, acid anhydrides, amines, amides, carbonates, sulfones, sulfonyl esters, phosphites, phosphates, nitriles, nitro, aldehydes, acetates, $SF_5$, or fluorocarbons (e.g., $—CF_3$, $—CF_2CF_3$).

In further embodiments, the non-aqueous solvent is a mixture of a first non-aqueous fluorine-containing solvent and a second non-aqueous, non-fluorine containing solvent. A ratio of amounts of the first solvent and the second solvent is greater than 1:2. For example, a ratio of amounts of the first solvent and the second solvent is selected from the range from 1:20 to 20:1 and, optionally, from 1:2 to 9:1. In another embodiment, the first solvent and the second solvent are each independently a polar solvent.

Non-Aqueous Solvent Mixtures Containing Mixtures of Fluoride Salts

In additional embodiments, non-aqueous solvent mixtures containing more than one fluoride salt are contemplated. For example, the solvent mixtures may include a first fluoride salt, a second fluoride salt, and one or more non-aqueous solvent. In some embodiment, for example, the first fluoride salt may include one or more fluoride ions and an organic cation, where the organic cation does not possess a carbon in the β-position or does not possess a carbon in the β-position having a bound hydrogen, and the cation charge center is N, P, S, or O. In some embodiment, for example, the second fluoride salt is different than the first fluoride salt and may include one or more fluoride ions and an organic cation, where the cation charge center is N, P, S, or O. In some embodiment, for example, the concentration of the fluoride ions dissolved in the electrolyte solution is greater than or equal to 0.05 M.

Processes and Reaction Mixtures for Fluoride-Ion Solvent Extraction

Solvent extraction is a technique for extracting a substance from one liquid into another liquid. In the context of aqueous and non-aqueous liquids, one mechanism of solvent extraction is ion exchange, where a first ion is transferred from the aqueous liquid to the organic liquid and a second ion is transferred from the organic liquid to the aqueous liquid.

Figure 2:
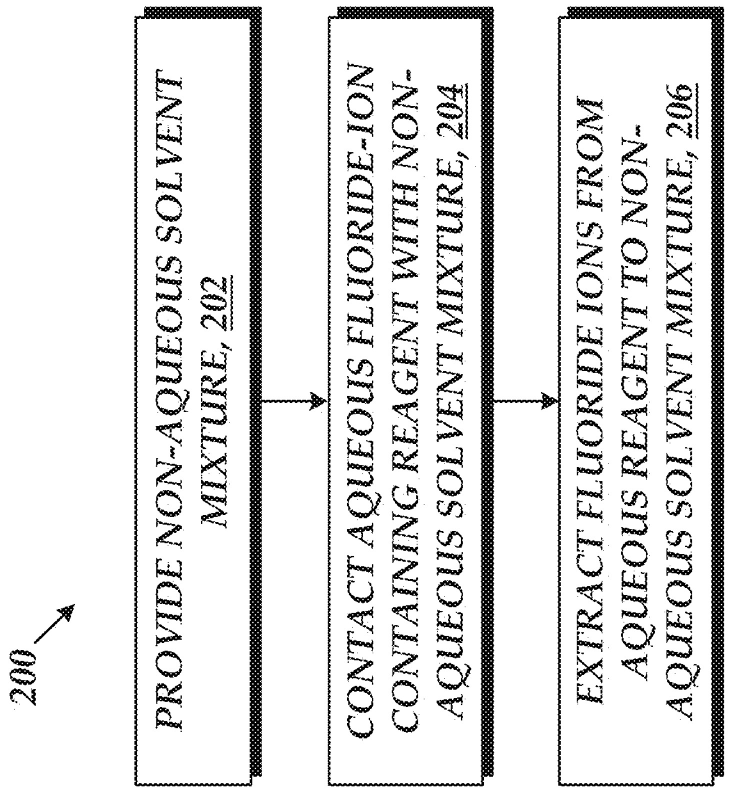
FIG. 2 is a schematic flow diagram illustrating an embodiment of a process for fluoride ion extraction employing non-aqueous salt solutions of the present disclosure.

With further reference to FIG. 2, an embodiment of a process 200 for solvent extraction to produce fluoride-ion containing solutions is provided. The process 200 includes providing a non-aqueous solvent mixture in step 202, contacting an aqueous, fluoride-ion containing reagent with the non-aqueous solvent mixture in step 204, and extracting fluoride ions from the aqueous reagent to the non-aqueous solvent mixture in step 206.

The non-aqueous solvent mixture includes a salt, where the salt includes a non-fluoride anion soluble in the non-aqueous solvent and an organic cation that does not possess a carbon in the β-position or does not possess a carbon in the β-position having a bound hydrogen, where the cation charge center is N, P, S, or O, as discussed above. In certain embodiments, the organic cation is selected from the group consisting of: (2,2-dimethylpropyl)trimethylammonium ($NpMe_3N^+$), bis(2,2-dimethylpropyl)dimethylammonium ($Np_2Me_2N^+$), and tris(2,2-dimethylpropyl)methylammonium ($Np_3MeN^+$). In further embodiments, the non-fluoride anion is selected from the group consisting of: hydroxide, alkoxide, iodide, acetate, carbonate, bicarbonate, sulfonate, arenesulfonate, alkylsulfonate, bis(trifluoromethylsulfonyl) imide (TFSI), triflate, trifluoroacetate, and at least partially fluorinated or substituted analogs thereof. In further embodiments, the contacting step 206 produces a fluoride salt selected from the group consisting of $NpMe_3NF$, $Np_2Me_2NF$, and $Np_3MeNF$ dissolved in the non-aqueous solution. A representative fluoride ion extraction is discussed in greater detail below in the Examples.

Non-aqueous fluoride ion-containing solutions resulting from the solvent extraction possess a concentration of fluoride ions greater than or equal to 0.05 M. It may be understood that, in alternative embodiments, the process 200 may include greater or few steps and that the steps may be performed in a different order than that illustrated in FIG. 2.

Embodiments of the processes 100, 200 may be further employed for radiolabeling. For example, one or more fluoride ions of the processes 100, 200 may be a radioactive fluorine isotope (e.g., $^{18}F$) to provide one or more of radioactive fluoride salt solutions, radioactive fluorine-containing reaction products, radioactive fluorine-involving reaction intermediates, and radioactive fluorine-involving catalytic processes.

EXAMPLES

The following specific examples are given to illustrate the practice of embodiments of the disclosed anhydrous fluoride salts, fluoride-ion containing solutions, and processes employing such fluoride-ion containing solutions but are not to be considered as limiting in any way.

Example 1

Synthesis and Characterization of Anhydrous Neo-pentyl Ammonium Fluoride Salts Improved methods for synthesizing 10 gram-scale batches of two neo-pentyl ammonium fluoride anhydrous salts, (2,2-dimethylpropyl)trimethylammonium fluoride ($NpMe_3NF$) and bis(2,2-dimethylpropyl)dimethylammonium fluoride ($Np_2Me_2NF$), are discussed below.

(i) $NpMe_3NF$:

$NpMe_3NF$ is formed from a neo-pentylamine starting material ($C_5H_{13}N$) and the net reaction illustrated below (E1-1):

(E1-1)

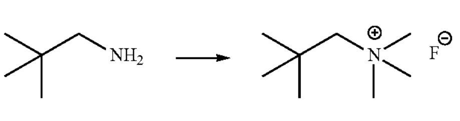

For example the neo-pentylamine is treated with formic acid and formaldehyde to form N,N,2,2-tetramethyl-1-propanamine (E1-1a):

(E1-1a)

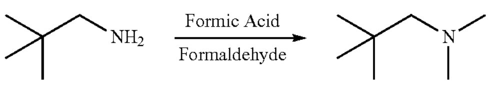

Subsequently, N,N,2,2-tetramethyl-1-propanamine is methylated by treatment with $CH_3I$ to form the ammonium salt $NpMe_3NI$ (E1-1b):

(E1-1b)

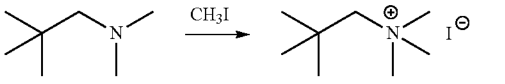

Alternatively, the neo-pentylamine may be exhaustively methylated by treatment with excess $CH_3I$, with $K_2CO_3$ and EtOH, followed by recrystallization from 2-propanol, to directly yield the ammonium salt $NpMe_3NI$ (E1-1a'):

(E1-1a')

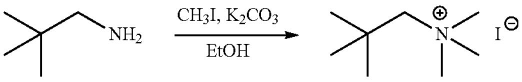

This latter synthesis route greatly reduces the reaction time and improves overall yield.

Subsequently, the iodine anion is replaced by a hydroxyl anion by reaction with $Ag_2O$ and $H_2O$ (E1-1c):

(E1-1c)

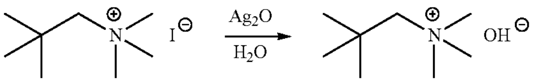

This reaction is run for one hour, then filtered and the filtrate used directly in the next reaction (E1-1d).

Finally, an HF titration procedure is followed to yield $NpMe_3NF$ (E1-1d):

(E1-1d)

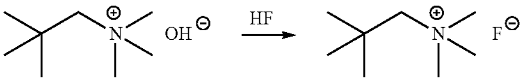

An azeotropic drying process was used, removing a majority of the water from the mixture using "benchtop" (i.e., not anhydrous) 2-propanol solvent on a rotary evaporator (3×). Subsequently, the mixture is filtered in a 2-propanol solution through a micron filter to remove a trace of gray impurity (presumably residual silver salt). After filtration, anhydrous 2-propanol is used to dry the remaining material by 5× azeotropic water removal. The resulting white powder is dried at 100° C. at about 80 mTorr for 5 days. To ensure purity and complete removal of trace amounts of water, the white powder was thoroughly crushed with a dry mortar and pestle in a glove box under an argon atmosphere. The finely crushed powder was transferred to a dry plastic bottle and then placed at about 80 mTorr for 7 days. The total yield of anhydrous $NpMe_3NF$ is about 10 g (88% from the iodide).

(ii) $Np_2Me_2NF$:

$Np_2Me_2NF$ is formed from the neo-pentylamine starting material ($C_5H_{13}N$) and the net reaction is illustrated below (E1-2):

(E1-2)

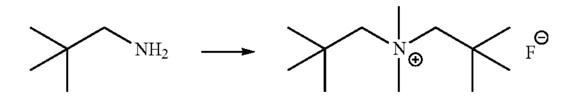

For example the neo-pentylamine is treated with trimethylacetyl chloride, chloroform ($CHCl_3$) and triethanolamine (TEA) to form N-neopentyl pivalamide (E2-2a):

(E1-2a)

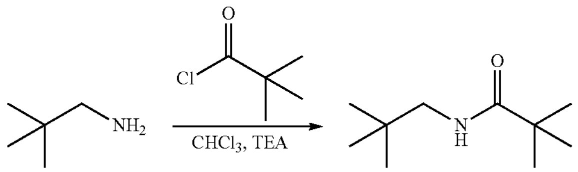

Subsequently, N-neopentyl pivalamide is treated with lithium aluminum hydride ($LiAlH_4$), n-butyl ether (n-Bu ether), and diethyl ether to form the secondary amine di-neopentyl amine (E1-2b):

(E1-2b)

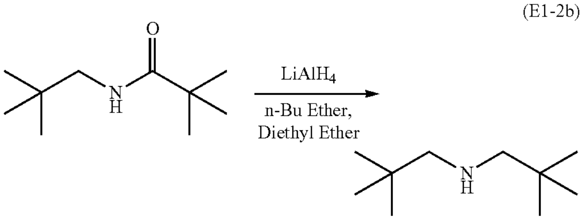

Methylation of di-neopentyl amine is performed for 6 days under reflux in acetonitrile to form the ammonium salt $Np_2Me_2NI$ (E1-2c):

(E1-2c)

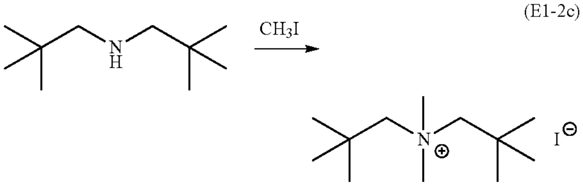

The modified post-titration drying procedure described above is also followed here to convert the $Np_2Me_2NI$ to $Np_2Me_2NF$ (E1-2d), (E1-2e):

(E1-2d)

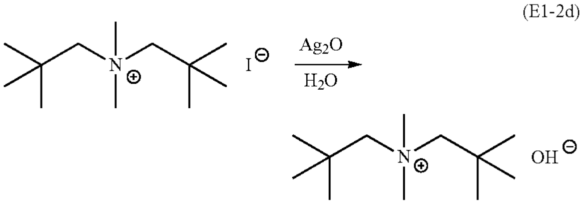

(E1-2e)

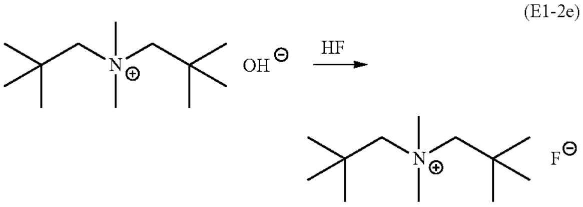

The total yield of anhydrous $Np_2Me_2NF$ is about 10 g (87% from the iodide).

Figure 4A:
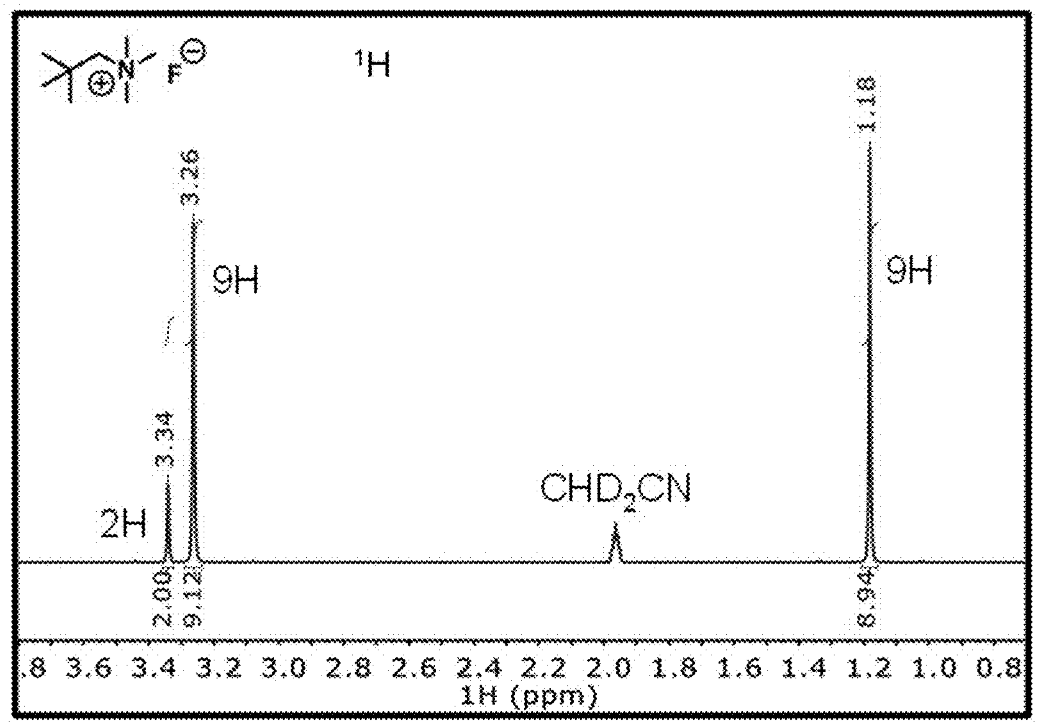
FIGS. 4A-4B are $^1H$ and $^{19}F$ NMR spectra of the product of an embodiment of a proposed synthesis route for preparation of (2,2-dimethylpropyl)trimethylammonium fluoride ($NpMe_3NF$)
Figure 4B:
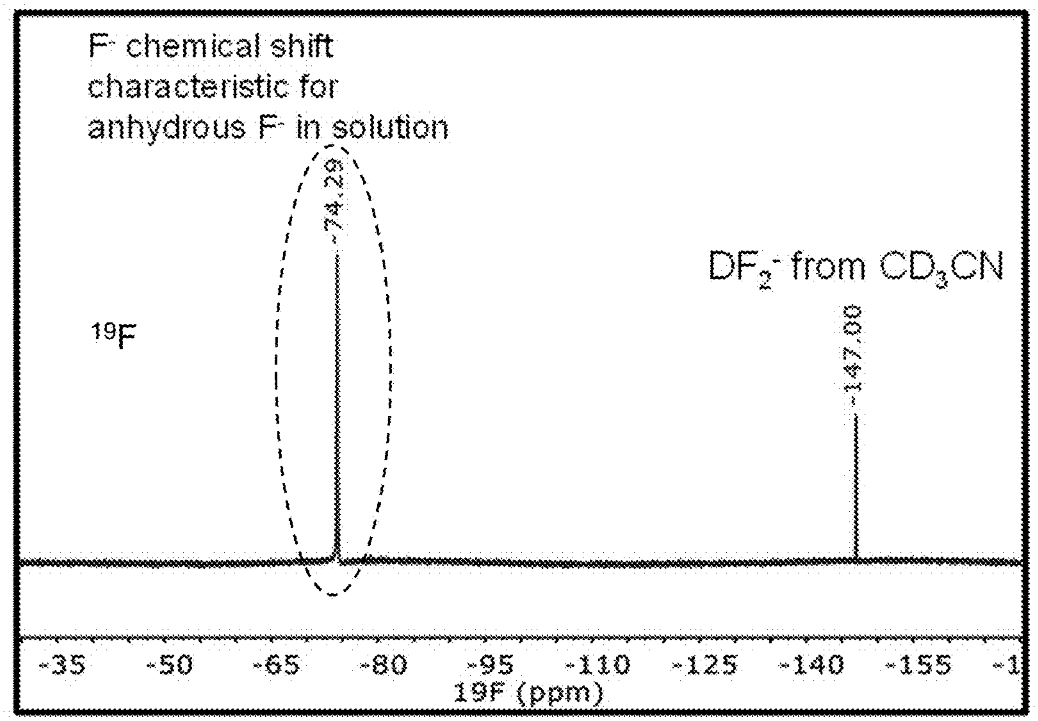

(iii) NMR Characterization:

The synthesized $NpMe_3NF$ and $Np_2Me_2NF$ salts are characterized by $^1H$ and $^{19}F$ NMR spectroscopy, respectively, in deuterated acetonitrile ($CD_3CN$). The measured NMR spectra for $NpMe_3NF$ are illustrated in FIGS. 4A-4B. The measured NMR spectra for $Np_2Me_2NF$ are illustrated in FIGS. 5A-5B.

Figure 5A:
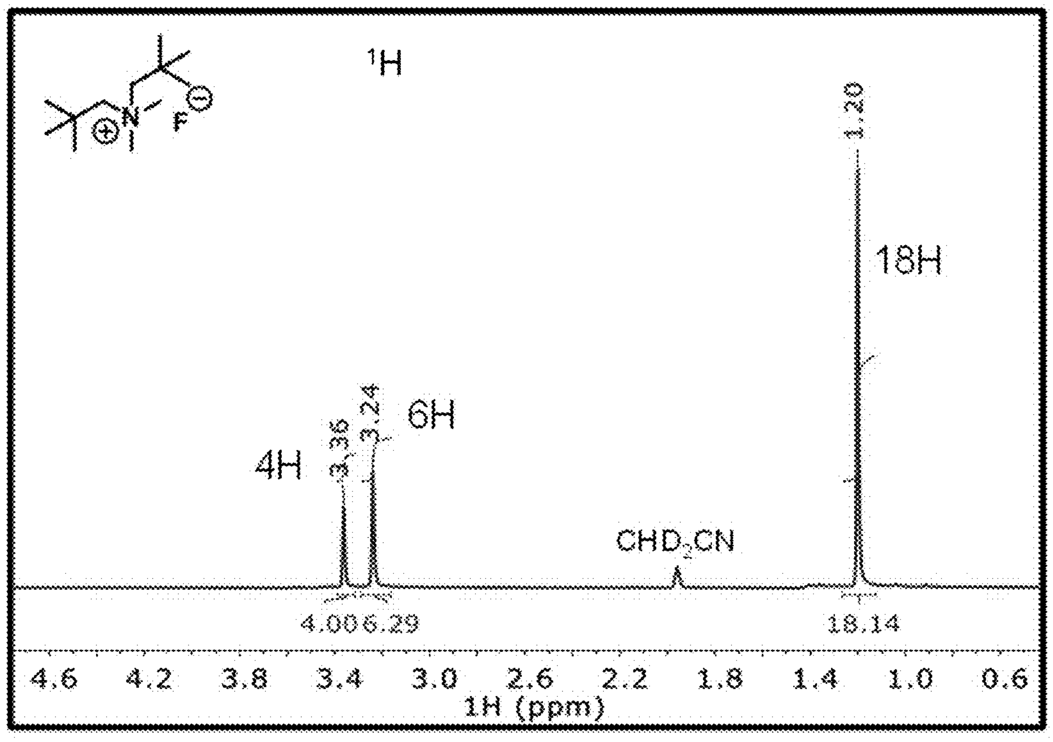
FIGS. 5A-5B are $^1H$ and $^{19}F$ NMR spectra of the product of an embodiment of a proposed synthesis route for preparation of and bis(2,2-dimethylpropyl)dimethylammonium fluoride ($Np_2Me_2NF$)
Figure 5B:
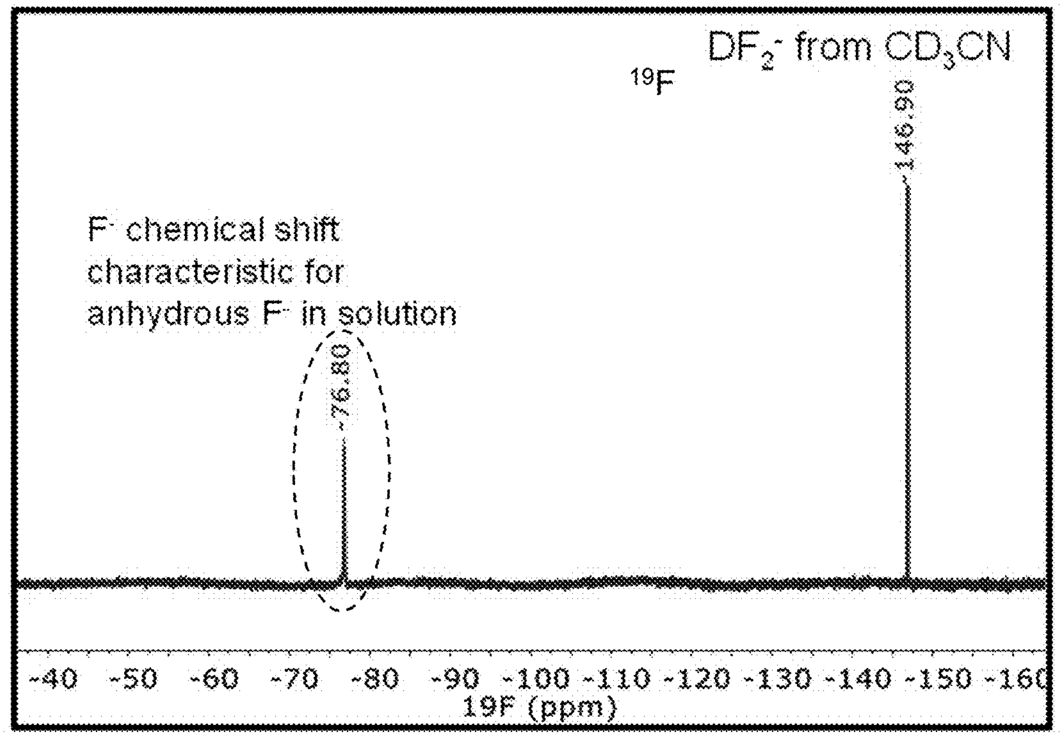
Figure 6A:
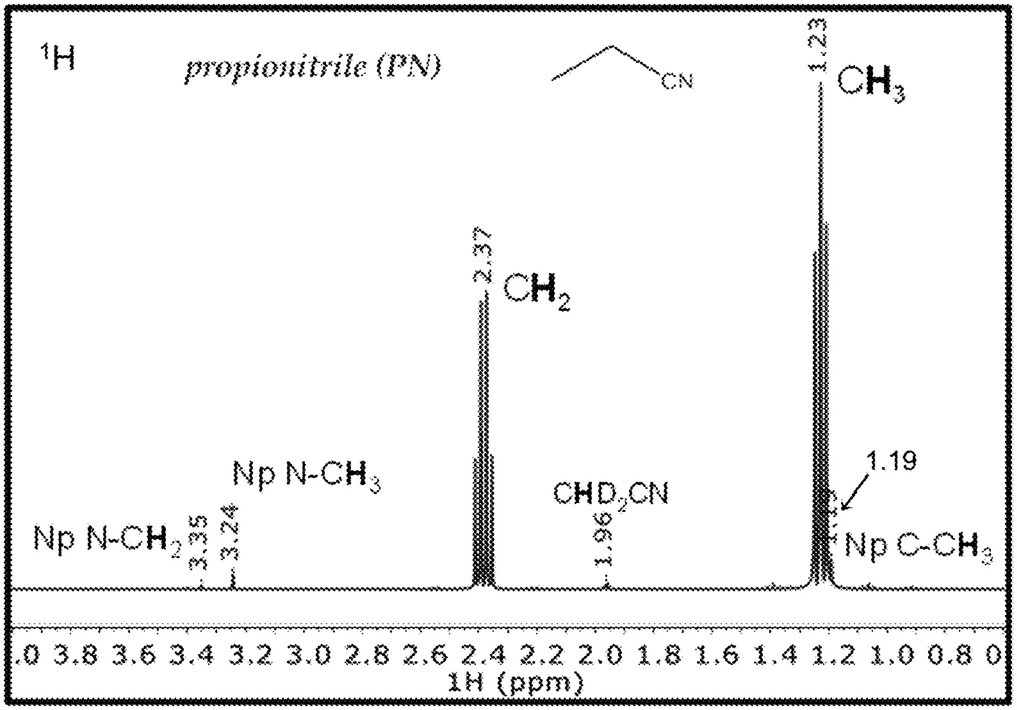
FIGS. 6A-6B are $^1H$ and $^{19}F$ NMR spectra of a solution of $NpMe_3NF$ and propionitrile (PN)
Figure 6B:
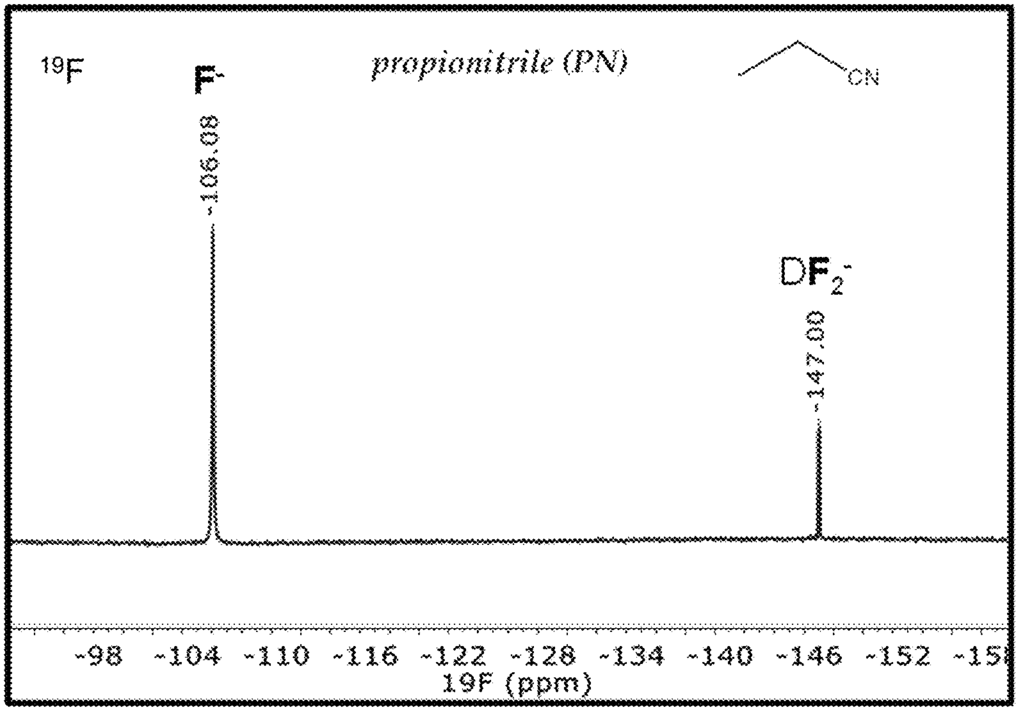
Figure 7A:
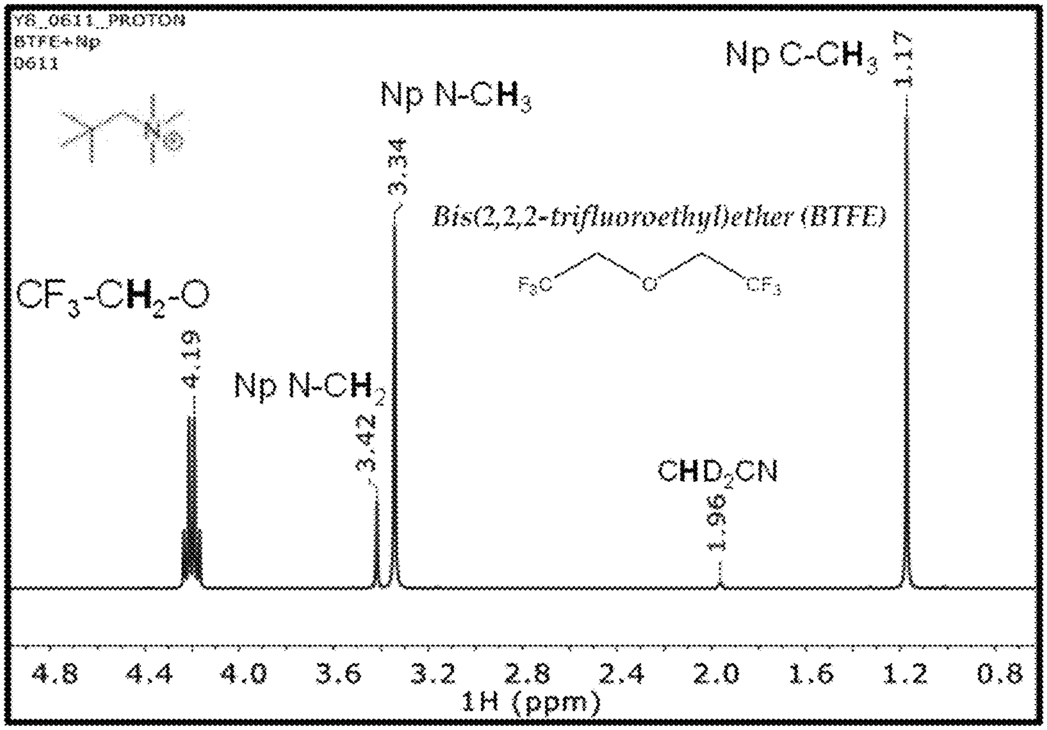
FIGS. 7A-7B are $^1H$ and $^{19}F$ NMR spectra of a solution of $NpMe_3NF$ and bis(2,2,2-trifluoroethyl)ether (BTFE)
Figure 7B:
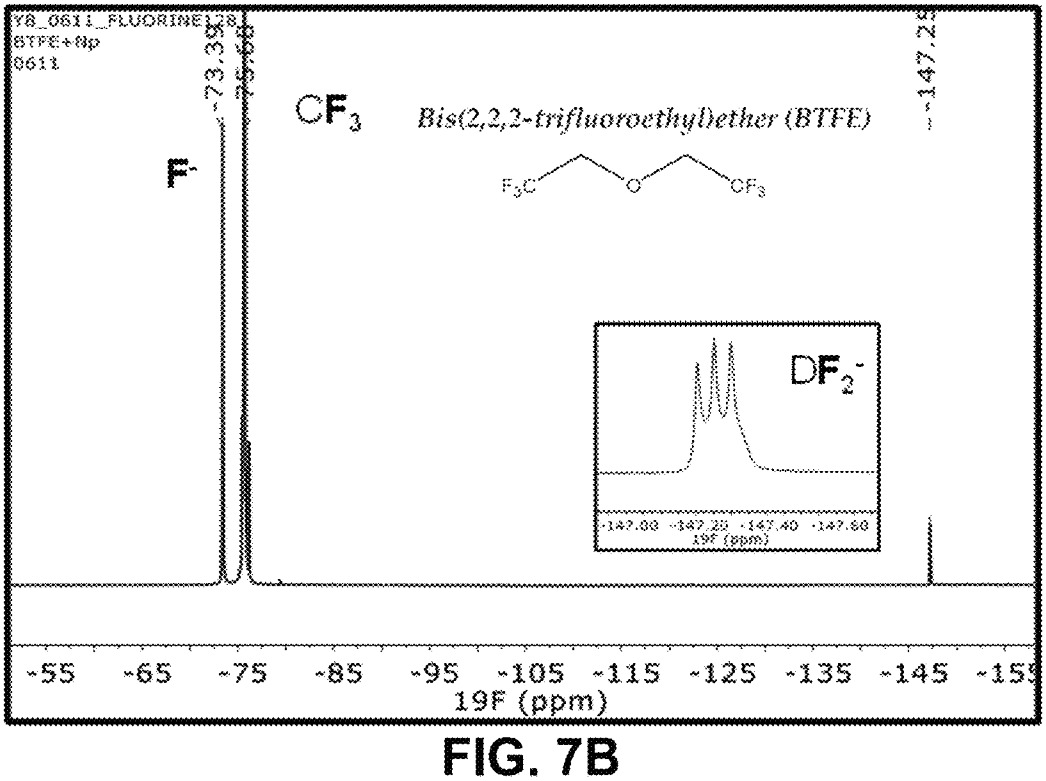
Figure 8A:
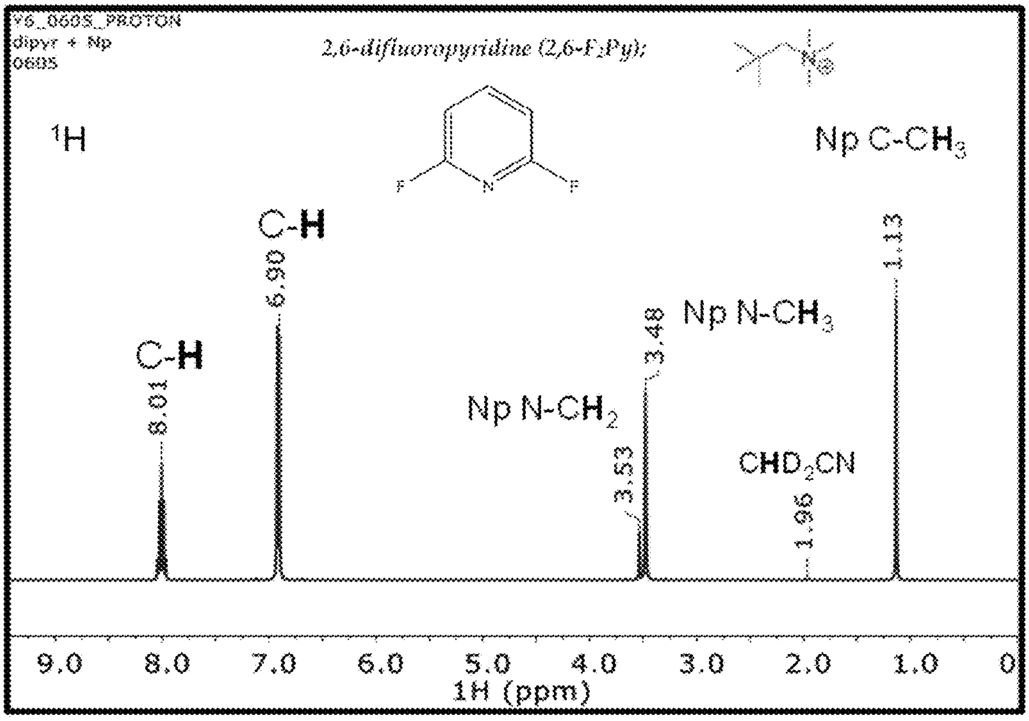
FIGS. 8A-8B are $^1H$ and $^{19}F$ NMR spectra of a solution of $NpMe_3NF$ and 2,6-difluoropyridine (2,6-$F_2$Py)
Figure 8B:
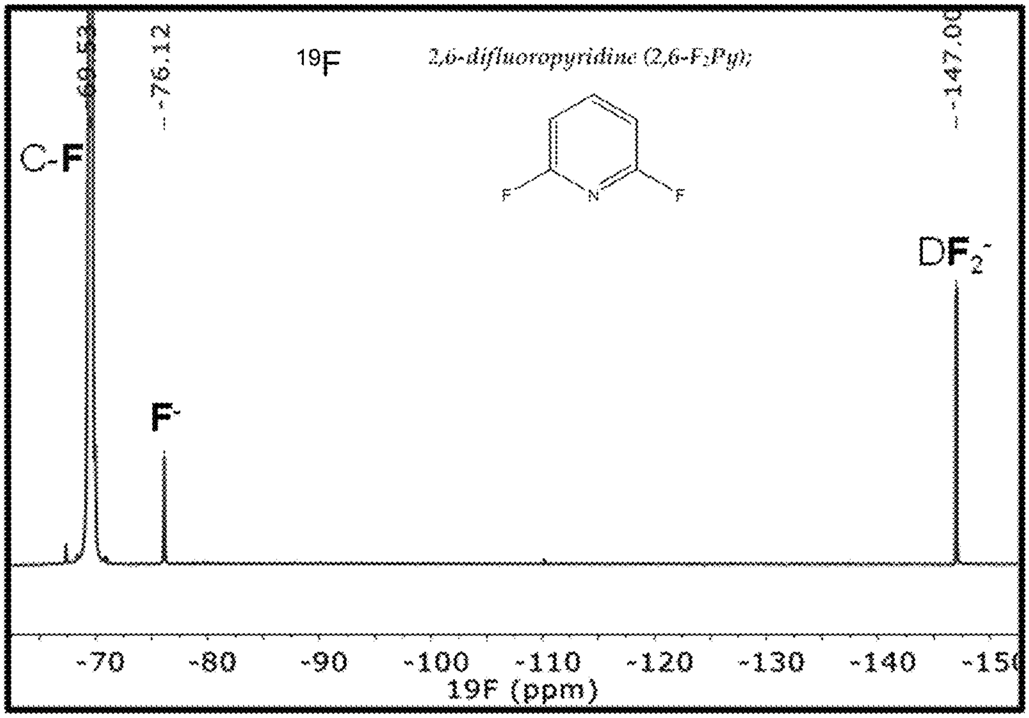
Figure 9A:
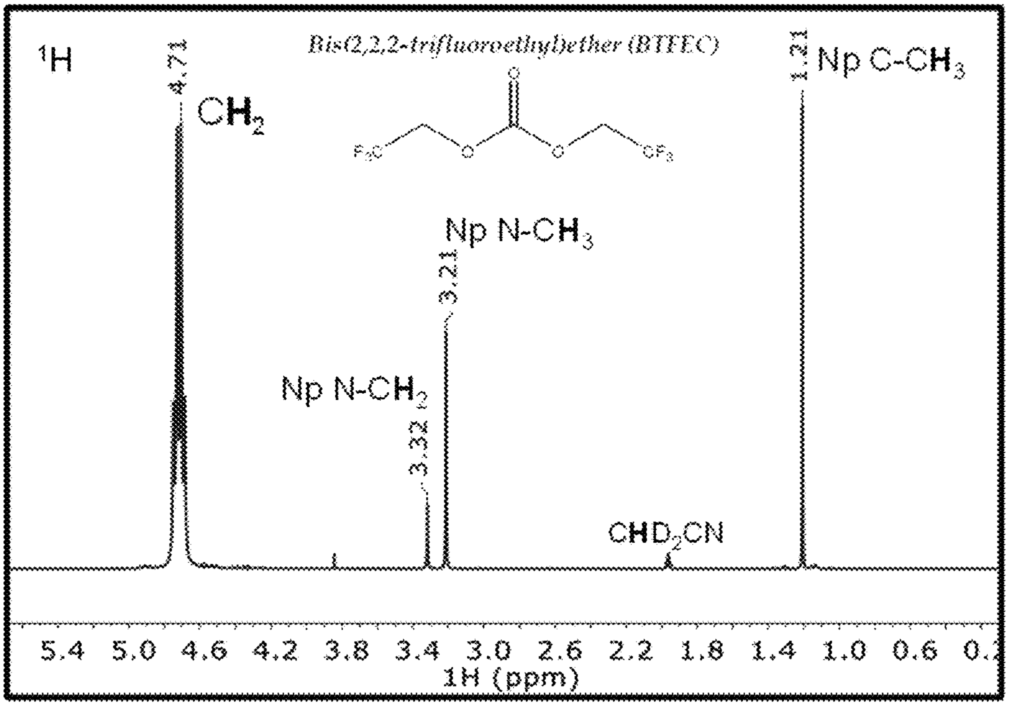
FIGS. 9A-9B are $^1H$ and $^{19}F$ NMR spectra of a solution of $NpMe_3NF$ and Bis(2,2,2-trifluoroethyl) carbonate (BTFEC)
Figure 9B:
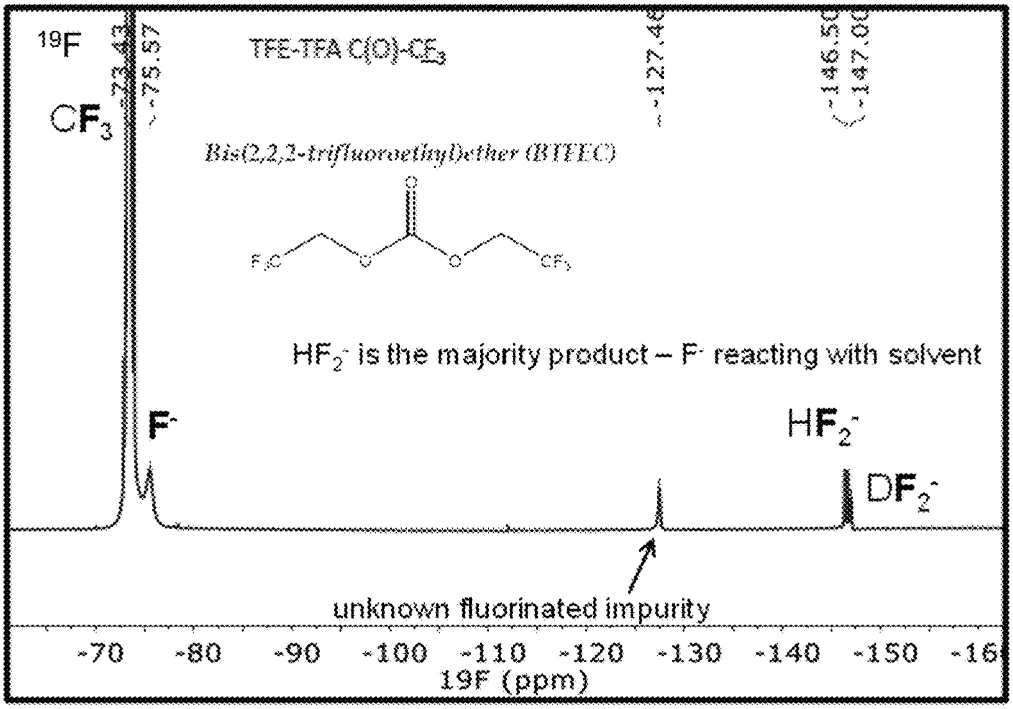
Figure 10A:
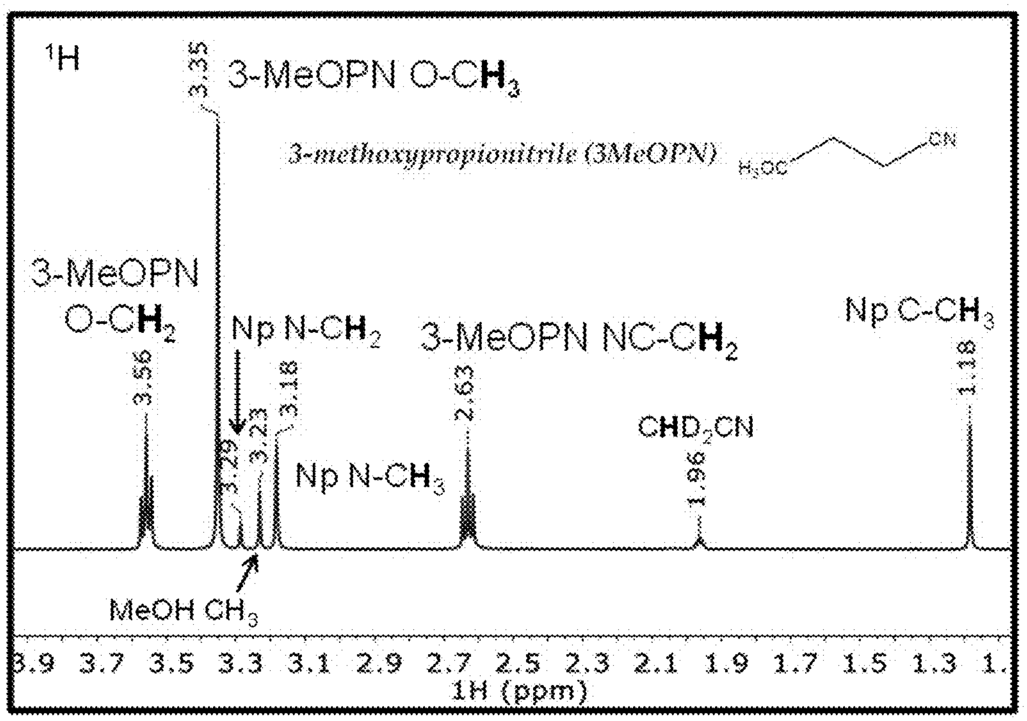
FIGS. 10A-10B are $^1H$ and $^{19}F$ NMR spectra of a solution of $NpMe_3NF$ and 3-methoxypropionitrile (3-MeOPN)
Figure 10B:
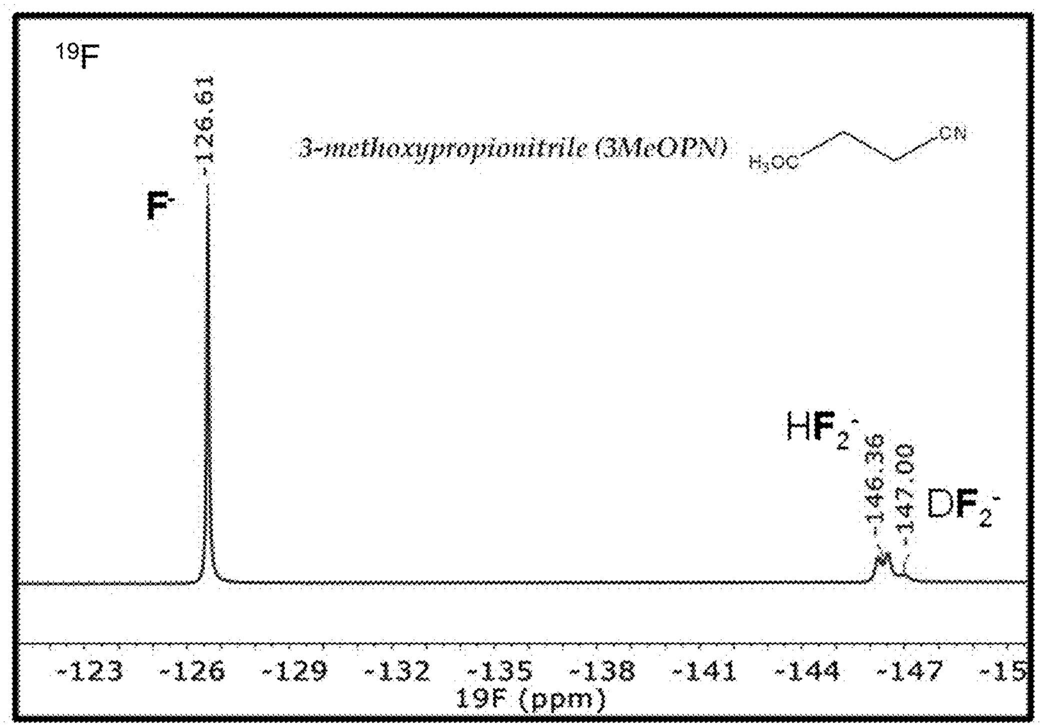

With reference to the $^1H$ spectra illustrated in FIGS. 4A, 5A, it is observed that the synthesized $NpMe_3NF$ and $Np_2Me_2NF$ salts are free from major impurities With reference to the $^{19}F$ spectra illustrated in FIGS. 4B, 5B, the $F^-$ chemical shift characteristic for anhydrous $F^-$ in $CD_3CN$ solution is observed in each case.

Example 2

Solvent Screening Using $NpMe_3NF$

Solubility and stability of $NpMe_3NF$ in various solvent classes is screened and the results are presented below in Table 2. $NpMe_3NF$ is determined to be soluble in a given solvent if the concentration of $NpMe_3NF$ dissolved within the solvent is greater than 0.05 M.

(i) $NpMe_3NF$ Solubility:

TABLE 2

Solubility of $NpMe_3NF$ in various non-aqueous solvents

| Solvent | Approximate Solubility (Mol/L) |
|---|---|
| 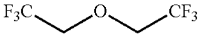 bis(2,2,2-trifluoroethyl)ether (BTFE) | 19.31 |
| 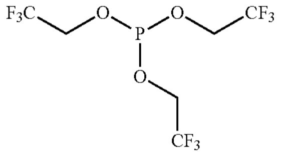 [SMILES: FC(F)(F)COP(OCC(F)(F)F)OCC(F)(F)F] Tris(2,2,2-trifluoroethyl)phosphite (TTFP) | 1.05 |

TABLE 2-continued

Solubility of $NpMe_3NF$ in various non-aqueous solvents

| Solvent | Approximate Solubility (Mol/L) |
|---|---|
| 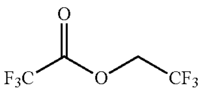 2,2,2-trifluoroethyl trifluoroacetate (TFE-TFA) | 0.95 |
| 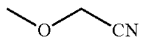 methoxyacetonitrile (MeOAN) | 0.80 |
| 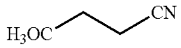 3-methoxypropionitrile (3-MeOPN) | 0.78 |
| 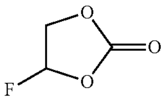 Fluoroethylene carbonate (FEC) | 0.71 |
| 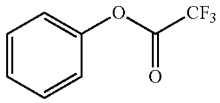 [SMILES: O=C(Oc1ccccc1)C(F)(F)F] phenyl trifluoroacetate (PhTFA) | 0.47 |
| 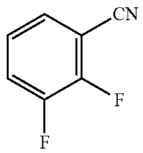 2,3-difluorobenzonitrile (2,3-$F_2$BN) | 0.40 |
| 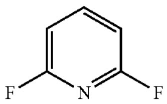 2,6-difluoropyridine (2,6-$F_2$Py) | 0.39 |
| 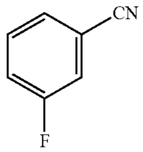 3-fluorobenzonitrile (3-FBN) | 0.19 |
| 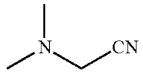 (Dimethylamino)acetonitrile (DMAN) | 0.14 |

TABLE 2-continued

Solubility of $NpMe_3NF$ in various non-aqueous solvents

| Solvent | Approximate Solubility (Mol/L) |
|---|---|
| 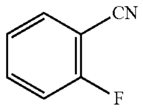 2-fluorobenzonitrile (2-FBN) | 0.12 |
| 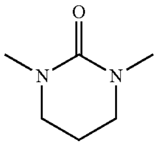 1,3-Dimethyl-3,4,5,6-tetrahydro-2(1H)-pyrimidinone (DMPU) | 0.11 |
| 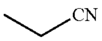 Propionitrile (PN) | 0.07 |

On review of the results of Table 2, it is observed that the solvents providing the highest $NpMe_3NF$ solubility are fluorinated solvents (i.e., BTFE, TTFP, TFE-TFA). Furthermore, the solubility of $NpMe_3NF$ BTFE is very large. Approximately 0.195 g $NpMe_3NF$ (1.3 mmol) is found to dissolve in 0.95 g BTFE (0.068 mL), indicating that $NpMe_3NF$ has an approximate solubility in BTFE above 19M (19.31M). Furthermore, the solubility of $NpMe_3NF$ in BTFE is significantly higher than that of the other solvents examined.

(ii) Solubility Comparison: TMAF Vs. $NpMe_3NF$ and $Np_2Me_2NF$

Further comparisons between the solubility of TMAF, $NpMe_3NF$, and $Np_2Me_2NF$ are performed using the fluorinated solvents 3-fluorobenzonitrile and BTFE, illustrated in Tables 3 and 4.

TABLE 3

Solubility of TMAF, $NpMe_3NF$, and $Np_2Me_2NF$ in 3-fluorobenzonitrile

| Salt | Structure | Solubility in 3-fluoro-benzonitrile | Solubility vs. TMAF |
|---|---|---|---|
| TMAF | 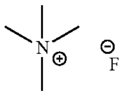 | 0.03M | |
| $NpMe_3NF$ | 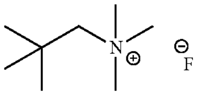 | 0.19M | >6x |
| $Np_2Me_2NF$ | 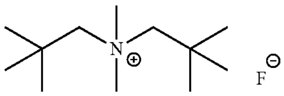 | 0.34M | >10x |

TABLE 4

| Solubility of TMAF and $NpMe_3NF$ in BTFE | |
|---|---|
| Salt | Solubility in BTFE |
| TMAF | trace |
| $NpMe_3NF$ | 19.3M |

It is observed that TMAF is not soluble in these fluorinated solvents at useful concentrations (e.g., >0.05 M). In contrast, $NpMe_3NF$ and $Np_2Me_2NF$ exhibit significantly higher solubility. These results indicate that the combination of a fluoride salt with a fluoride-containing cation and fluorinated solvents is needed to obtain high solubility in non-aqueous solvents.

(iii) $NpMe_3NF$ Stability:

$NpMe_3NF$ stability in various solvents is analyzed by $^1H$ and $^{19}F$ NMR measurements. Preliminary criteria used for a solvent being "chemically stable" to the $F^-$ ion are observation of a clear, sharp peak in the $^{19}F$ spectrum, alongside a 1:1:1 triplet arising from the $DF_2^-$ formation from the deuterated acetonitrile solvent ($CD_3CN$). The corresponding $^1H$ and $^{19}F$ NMR spectra are illustrated in FIGS. 6-10, It is observed that propionitrile (PN), BTFE, and 2,6-difluoropyridine (2,6-$F_2$Py), exhibited good stability. In contrast, for example, Bis(2,2,2-trifluoroethyl) carbonate (BTFEC) and 3-methoxypropionitrile (3-MeOPN) exhibited poor stability.

Example 3

Theoretical Modeling of Fluoride-solvent Interaction

Theoretical modeling is performed to better understand the nature of the interaction between the above-identified quaternary alkylammonium fluoride salts and solvents giving rise to enhanced solubility. Fluoride salts TMAF, $NpMe_3NF$, and $Np_2Me_2NF$ and a range of substituted alkyl- and benzylammonium salts in BTFE, glymes, and related solvents are investigated.

Figure 11:
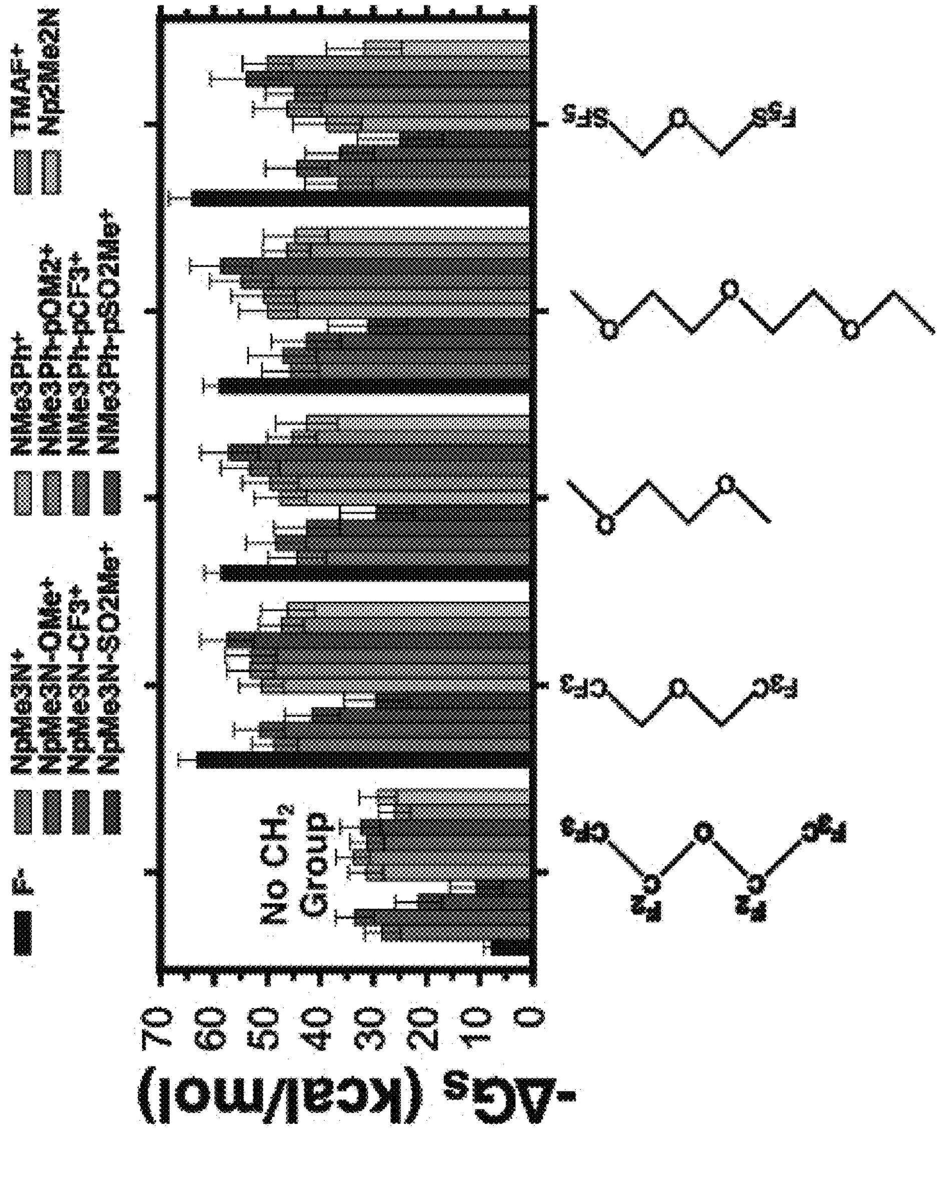
FIG. 11 is a plot of calculated solvation free energy ($\Delta G_s$) for fluoride ion and different cations in solvents with and without a positively polarized $CH_2$ moiety.

(i) Solvation Free Energy:

Calculated solvation free energies ($\Delta G_s$) for fluoride and several cations in solvents (i) without a positively polarized $CH_2$ moiety in the solvent (leftmost solvents) and (ii) solvents with a positively polarized $CH_2$ moiety in the solvent (i.e., characterized by the form [X—$(CH_2)_n$—Y], where n=1 or 2) are shown in FIG. 11. The solvation free energy is calculated as a transfer free energy from vacuum into the solvent using the thermodynamic integration method.

With reference to solvents that lack a $CH_2$ moiety, removal of $CH_2$ moiety is observed to result in a tremendous decrease in fluoride salt solubility. Conversely, solvents characterized by the form X—$CH_2$—Y—$CH_2$—X and X—$CH_2CH_2$—Y—$CH_2CH_2$—X exhibit up to a ten-fold increase in the calculated fluoride solvation free energy, as compared to solvents structures lacking $CH_2$ moieties adjacent to electron withdrawing groups. These simulations illustrate that the relative increase in fluoride solvation due to the fluoride:$CH_2$ interaction and how this may be modulated by appropriate substitution in the cation molecular structure.

Figure 12B:
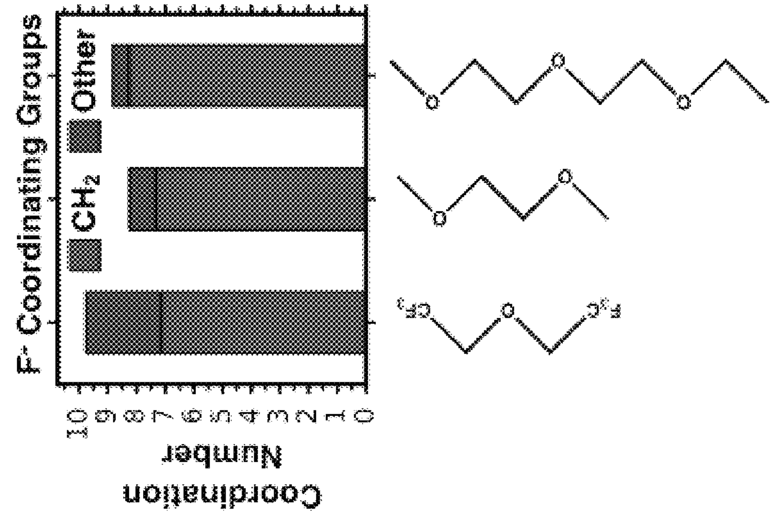
FIG. 12B is a plot of fluoride ion coordination number as a function of solvent for BTFE, 1,2-dimethoxyethane, and 1-ethoxy-2-(methoxyethoxy)ethane.
Figure 12A:
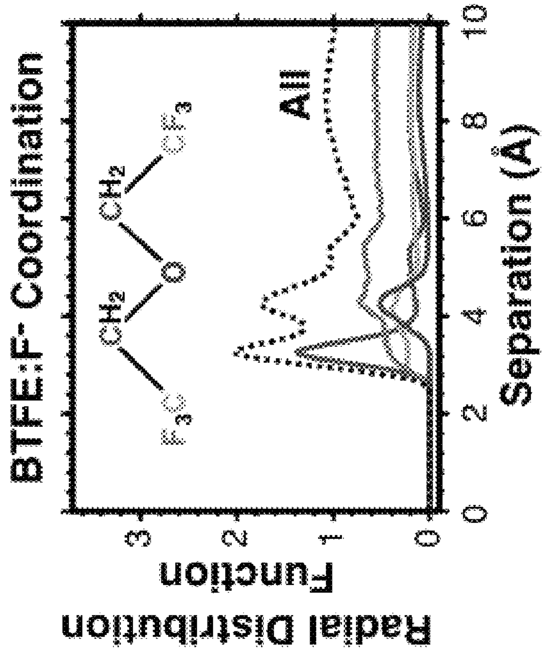
FIG. 12A is a plot of radial distribution function as a function of separation for fluoride ions in a BTFE solvent at dilute concentration.
Figure 13:
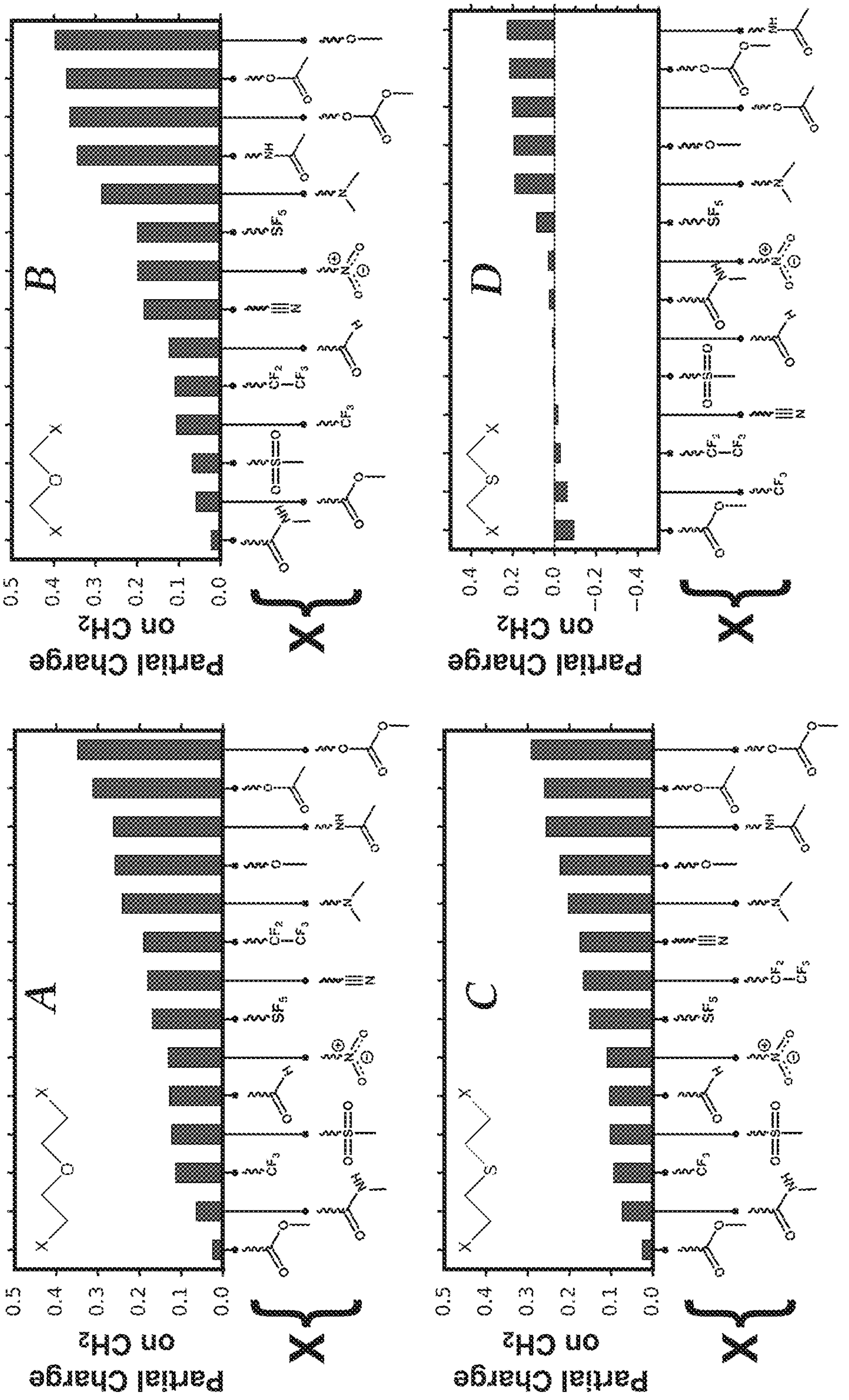
FIGS. 13, A-D are plots of partial charge on $CH_2$ in various solvent molecules characterized by the form X—$CH_2$—Y—$CH_2$—X and X—$CH_2$—$CH_2$—Y—$CH_2$—$CH_2$—X.

(ii) Molecular Dynamics Simulations:

Molecular dynamics simulations of fluoride in a range of solvents are performed to determine statistically averaged fluoride coordination structures, as shown in FIGS. 12A-12B. With reference to FIG. 12A, the radial distribution function for BTFE:$F^-$ coordination shows which groups are present at various displacements from the fluoride and demonstrates the majority presence of $CH_2$ in the first coordination shell.

With reference to FIG. 12B, simulation results calculating the average number of non-hydrogen atoms in the first fluoride coordination shell in several solvents (BTFE, 1,2-dimethoxyethane, and 1-ethoxy-2-(methoxyethoxy)ethane) are presented. Examining the structure of BTFE, it may be observed that each $CH_2$ group is adjacent one oxygen and one $CF_3$ group. In contrast, in both 1,2-dimethoxyethane and 1-ethoxy-2-(methoxyethoxy)ethane, the $CH_2$ group is adjacent two oxygens, with the 1-ethoxy-2-(methoxyethoxy) ethane possessing an additional oxygen and two additional methylene adjacent thereto, as compared to 1,2-dimethoxyethane. In general, both the $CF_3$ group and oxygen are electron-withdrawing, In the case of each solvent, there is a significant preferential association of fluoride with $CH_2$, as compared to other functional groups, as evidenced by the coordination number of $CH_2$ (~7-8) being higher than that that for all other functional groups combined (~1-3). This observation supports the proposition that association of fluoride with $CH_2$ is promoted by the presence of electron-withdrawing groups adjacent the $CH_2$ groups. This observation further allows for rational choice of the solvent or solvent mixture to improved fluoride salt solubility.

(iii) Partial Charge Analysis:

Partial atomic charges on $CH_2$ groups are further investigated for solvent molecules characterized by the form X—$CH_2$—Y—$CH_2$—X and X—$CH_2$—$CH_2$—Y—$CH_2$—$CH_2$—X, where X and Y are electron withdrawing groups having a combined effect to confer a partial positive charge on the $CH_2$ group or groups, to explore this hypothesis. Y is O or S and X is a functional group selected from ethers, esters, acid anhydrides, amines, amides, carbonates, sulfones, sulfonyl esters, phosphites, phosphates, nitriles, nitro, aldehydes, acetates, $SF_5$, or fluorocarbons (e.g., —$CF_3$, —$CF_2CF_3$). The partial charges are calculated using the CHELPG algorithm with density functional theory calculated electron densities (B3LYP/def2-PVTZ level of theory) and are illustrated in FIGS. 13A-13D.

It is observed that solvent molecules characterized by the form X—$CH_2$—Y—$CH_2$—X and X—$CH_2$—$CH_2$—Y—$CH_2$—$CH_2$—X consistently exhibit increased positive charge on the $CH_2$ moieties. In conjunction with the above theoretical results, this demonstrates that positively charged $CH_2$ groups mediate fluoride coordination and dissolution in a particular solvent or solvent mixture across a wide variety of electron withdrawing units.

Example 4

Non-Aqueous Fluoride Salt Solutions as Reagents for Organic Synthesis (i) Nucleophilic Substitution High concentration of fluorides in non-aqueous solvents may be employed for organic synthesis (e.g., >19M in BTFE). In particular, such high fluoride ion concentrations may provide control over product distribution and/or high rates of reaction. As an illustrative example, reaction products arising from nucleophilic substitution of an organic compound (1-bromooctane) with fluorine using $NpMe_3NF$ as a source of nucleophilic $F^-$ is compared using two different $NpMe_3NF$ solutions.

The first solution contains $NpMe_3NF$ in non-anhydrous, deuterated acetonitrile ($CD_3CN$) (E4-1), (E4-2):

(E4-1)

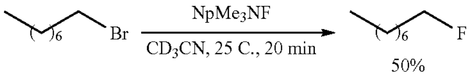

(E4-2)

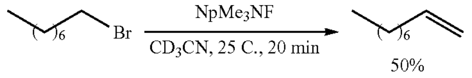

It is observed that the substitution product (E4-1) and elimination product (E4-2) are produced in equal amounts in non-anhydrous, deuterated acetonitrile.

The second source of nucleophilic fluoride ions is a solution of $NpMe_3NF$ in BTFE, according to embodiments of the disclosure (E4-3), (E4-4):

(E4-3)

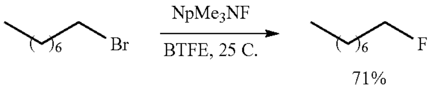

(E4-4)

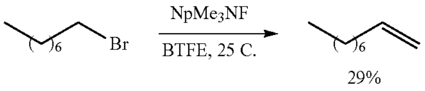

In contrast with non-anhydrous, deuterated acetonitrile, the solution containing anhydrous BTFE yields a greater abundance of the substitution product (E4-3) over the elimination product (E4-4). This result demonstrates that the greater activity of $F^-$ as a nucleophile in BTFE, as compared to acetonitrile. This result demonstrates that the combination of fluoride salt and solvent in the non-aqueous solvent mixtures can tailor the concentration of reactive fluoride ions in the non-aqueous solvent mixture and drive the reaction towards a desired product.

Example 5

Fluoride Ion Extraction

Current processes for making $^{18}F$-labeled species for positron emission tomography (PET) treatments are inconvenient and expensive. For example, state-of-the-art processes involve multiple steps (E5-1):

(E5-1)

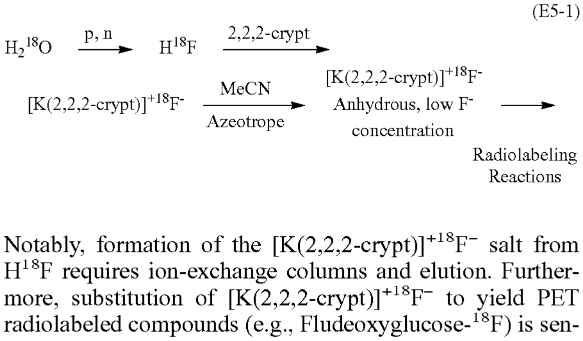

Notably, formation of the $[K(2,2,2\text{-crypt})]^{+18}F^-$ salt from $H^{18}F$ requires ion-exchange columns and elution. Furthermore, substitution of $[K(2,2,2\text{-crypt})]^{+18}F^-$ to yield PET radiolabeled compounds (e.g., Fludeoxyglucose-$^{18}F$) is sensitive to side reactions caused by the presence of competing nucleophiles, such as $OH^-$, present under non-anhydrous conditions. Accordingly, further steps are required to form anhydrous $[K(2,2,2\text{-crypt})]^{+18}F^-$ to avoid side-reactions.

In contrast, embodiments of process 200 may be employed to extract radioactive fluoride ions (e.g., $^{18}F^-$) to give, in a single step, a high concentration of non-aqueous fluoride salt that is useful for synthesis of PET radiolabeled compounds (E5-2):

(E5-2)

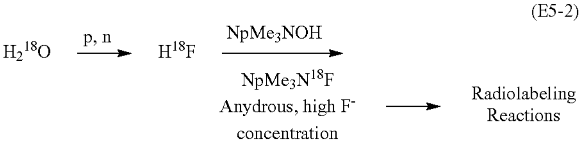

The high solubility of the fluoride salt in BTFE, or other non-aqueous solvents, as discussed above, may serve to concentrate the $^{18}F$ species, while enabling its straightforward use in organic synthesis applications (e.g., nucleophilic reactions) under anhydrous conditions.

While E5-2 illustrates use of $NpMe_3NOH$ as an anhydrous salt precursor, any salt formed from combinations of cations and non-fluoride anions discussed above with regards to process 200 may be employed (e.g., $NpMe_3NI$). In further embodiments, salt precursors that cannot be prepared anhydrous in fluoride form may be employed at room temperature or above (e.g., $^nBu_4NI$, $^nBu_4NOH$).

Statements Regarding Chemical Compounds and Nomenclature

As used herein, the term “group” may refer to a functional group of a chemical compound. Groups of the present compounds refer to an atom or a collection of atoms that are a part of the compound. Groups of the present compounds may be attached to other atoms of the compound via one or more covalent bonds. Groups may also be characterized with respect to their valence state. The present compounds includes groups characterized as monovalent, divalent, trivalent, etc. valence states.

As used herein, the term “substituted” refers to a compound where a hydrogen is replaced by another functional group.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure including 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups where the alky portion of the groups is substituted as provided herein in connection with the description of alkyl groups. As used herein MeO— refers to $CH_3O$—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those that are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6-, 7- or 8-member aromatic rings, including heterocyclic aromatic rings. The term heteroaryl specifically refers to aryl groups having at least one 5-, 6-, 7- or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein provided in a covalently bonded configuration in the compounds of the disclosure at any suitable point of attachment. In embodiments, aryl groups contain between 5 and 30 carbon atoms. In embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups where the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups where the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As used herein, the terms "alkylene" and "alkylene group" are used synonymously and refer to a divalent group derived from an alkyl group as defined herein. The present disclosure may include compounds having one or more alkylene groups. Alkylene groups in some compounds function as attaching and/or spacer groups. Compounds of the present disclosure may have substituted and/or unsubstituted $C_1$-$C_{20}$ alkylene, $C_1$-$C_{10}$ alkylene and $C_1$-$C_5$ alkylene groups.

As used herein, the terms "cycloalkylene" and "cycloalkylene group" are used synonymously and refer to a divalent group derived from a cycloalkyl group as defined herein. The present disclosure may include compounds having one or more cycloalkylene groups. Cycloalkyl groups in some compounds function as attaching and/or spacer groups. Compounds of the present disclosure may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The present disclosure may include compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Non-limiting examples include substituted and/or unsubstituted $C_3$-$C_{30}$ arylene, $C_3$-$C_{20}$ arylene, $C_3$-$C_{10}$ arylene and $C_1$-$C_5$ arylene groups.

As used herein, the terms "heteroarylene" and "heteroarylene group" are used synonymously and refer to a divalent group derived from a heteroaryl group as defined herein. The present disclosure may include compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Non-limiting examples include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The present disclosure may include compounds having one or more alkenylene groups. Alkenylene groups in some compounds function as attaching and/or spacer groups. Non-limiting examples include substituted and/or unsubstituted $C_2$-$C_{20}$ alkenylene, $C_2$-$C_{10}$ alkenylene and $C_2$-$C_5$ alkenylene groups.

As used herein, the terms "cylcoalkenylene" and "cylcoalkenylene group" are used synonymously and refer to a divalent group derived from a cylcoalkenyl group as defined herein. The present disclosure may include compounds having one or more cylcoalkenylene groups. Cycloalkenylene groups in some compounds function as attaching and/or spacer groups. Non-limiting examples include substituted and/or unsubstituted $C_3$-$C_{20}$ cylcoalkenylene, $C_3$-$C_{10}$ cylcoalkenylene and $C_3$-$C_5$ cylcoalkenylene groups.

As used herein, the terms "alkynylene" and "alkynylene group" are used synonymously and refer to a divalent group derived from an alkynyl group as defined herein. The present disclosure may include compounds having one or more alkynylene groups. Alkynylene groups in some compounds function as attaching and/or spacer groups. Non-limiting examples include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group such as a fluoro (—F), chloro (—Cl), bromo (—Br), iodo (—I), or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings including carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)n-alkoxy where n is an integer from 1 to 10, preferably 1 to 4, and more preferably for some embodiments 1 to 3.

As to any of the groups described herein that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds. Optional substitution of alkyl groups includes substitution with one or more alkenyl groups, aryl groups or both, where the alkenyl groups or aryl groups are optionally substituted. Optional substitution of alkenyl groups includes substitution with one or more alkyl groups, aryl groups, or both, where the alkyl groups or aryl groups are optionally substituted. Optional substitution of aryl groups includes substitution of the aryl ring with one or more alkyl groups, alkenyl groups, or both, where the alkyl groups or alkenyl groups are optionally substituted.

Optional substituents for any alkyl, alkenyl and aryl group includes substitution with one or more of the following substituents, among others: halogen, including fluorine, chlorine, bromine or iodine; pseudohalides, including —CN;

—COOR, where R is a hydrogen or an alkyl group or an aryl group and more specifically where R is a methyl, ethyl, propyl, butyl, or phenyl group all of which groups are optionally substituted;

—COR, where R is a hydrogen or an alkyl group or an aryl group and more specifically where R is a methyl, ethyl, propyl, butyl, or phenyl group all of which groups are optionally substituted;

—$CON(R)_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—$OCON(R)_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—$N(R)_2$, where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring that can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—$SO_2R$, or —SOR, where R is an alkyl group or an aryl group and more specifically where R is a methyl, ethyl, propyl, butyl, or phenyl group, all of which are optionally substituted;

—OCOOR, where R is an alkyl group or an aryl group;

—$SO_2N(R)_2$, where each R, independently of each other R, is a hydrogen, or an alkyl group, or an aryl group all of which are optionally substituted and where R and R can form a ring that can contain one or more double bonds and can contain one or more additional carbon atoms;

—OR, where R is H, an alkyl group, an aryl group, or an acyl group all of which are optionally substituted. In a particular example R can be an acyl yielding —OCOR", where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (where XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process for chemical synthesis, comprising:

reacting a non-fluoride salt of an organic cation with hydrogen fluoride, thereby forming a fluoride salt of the organic cation, wherein the organic cation does not possess a carbon in the β-position or does not possess a carbon in the β-position having a bound hydrogen, and wherein the cation charge center is N, P, S, or O; and wherein the reaction of the non-fluoride salt of the organic cation with hydrogen fluoride is characterized by formula (E1-1d) or formula (E1-2e):

(E1-1d)

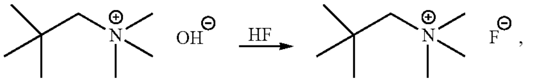

, or (E1-2e)

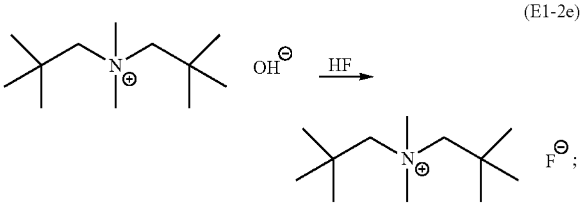

;

drying the fluoride salt of the organic cation; and dissolving the dried fluoride salt of the organic cation in one or more non-aqueous solvent, thereby forming a non-aqueous solvent mixture;

wherein a concentration of fluoride ions dissolved in said non-aqueous solvent mixture is greater than or equal to 0.05 M.

2. The process of claim 1, wherein said salt is provided to said non-aqueous solvent in an anhydrous form.

3. The process of claim 1, wherein said fluoride ions comprise a radioactive fluorine isotope.

4. The process of claim 1, wherein the concentration of the fluoride ions dissolved in said non-aqueous solvent mixture is selected over the range of 0.05 M to 20 M.

5. The process of claim 1, wherein a concentration of fluoride anions dissolved in said non-aqueous solvent mixture is selected over the range of 0.05 M to 20 M.

6. The process of claim 4, wherein said concentration of the fluoride ions is greater than or equal to 1 M and less than or equal to 20 M.

7. The process of claim 1, wherein the non-aqueous solvent comprises at least one functional group characterized by the form [X—$(CH_2)_n$—Y], where X and Y are polar functional groups having a combined effect to confer a partial positive charge on the $CH_2$ group or groups and n=1 or 2.

8. The process of claim 7, wherein Y is O or S and X is a functional group selected from the group consisting of ethers, esters, acid anhydrides, amines, amides, carbonates, sulfones, sulfonyl esters, phosphites, phosphates, nitriles, nitro, aldehydes, acetates, $SF_5$, or fluorocarbons.

9. The process of claim 1, wherein the non-aqueous solvent is a fluorinated ether or any combination thereof.

10. The process of claim 9, wherein the fluorinated ether is characterized by the formula (FX7a) or (FX7b), (FX7c), (FX7d), (FX7e), (FX7f), or (FX7g):

(FX7a)

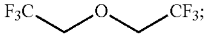

;

(FX7b)

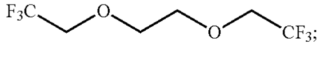

;

-continued (FX7c)

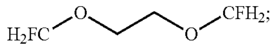

(FX7d)

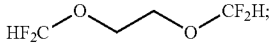

(FX7e)

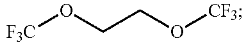

(FX7f)

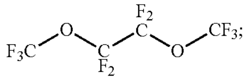

or (FX7g)

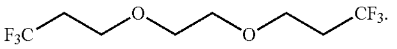

11. The process of claim 1, wherein the non-aqueous solvent is a fluorinated phosphite characterized by the formula (FX8a):

(FX8a)

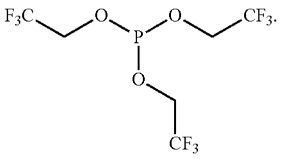

12. The process of claim 1, wherein the non-aqueous solvent is a fluorinated ester or anhydride or any combination thereof characterized by the formula (FX9a), (FX9b), or (FX9c):

(FX9a)

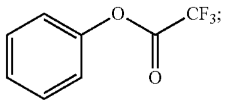

(FX9b)

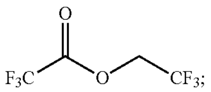

or (FX9c)

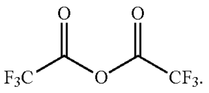

13. The process of claim 1, wherein the non-aqueous solvent is a nitrile or any combination thereof characterized by the formula (FX10a), (FX10b), (FX10c), or (FX10d):

(FX10a)

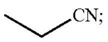

(FX10b)

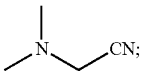

(FX10c)

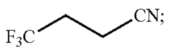

or

-continued (FX10d)

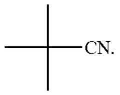

14. The process of claim 1, wherein the non-aqueous solvent is a fluorine-substituted aromatic solvent or any combination thereof is characterized by the formula (FX11a), (FX11b), (FX11c), or (FX11d):

(FX11a)

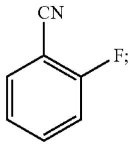

(FX11b)

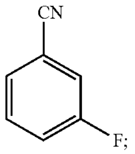

(FX11c)

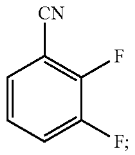

or (FX11d)

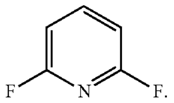

15. The process of 1, wherein the non-aqueous solvent is characterized by the formula (FX12a) or (FX12b) and any combination thereof:

(FX12a)

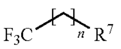

or (FX12b)

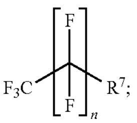

wherein $R^7$ is a substituted or unsubstituted $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_{20}$ alkyl, $C_2$-$C_{20}$ alkoxycarbonyl, halo, $C_4$-$C_{30}$ aliphatic, $C_4$-$C_{30}$ cycloaliphatic, or $C_4$-$C_{30}$ aromatic; and wherein n is an integer selected from the range of 1 to 20.

16. The process of claim 1, wherein the drying step comprises removing water from the fluoride salt of the organic cation.

17. The process of claim 1, wherein the drying step comprises an azeotropic drying process.

18. The process of claim 1, further comprising reacting an organic compound with the fluoride salt in the non-aqueous solvent mixture by nucleophilic substitution and elimination, thereby forming a mixture of a substitution product of the organic compound and an elimination product of the organic compound.

19. The process of claim 18, wherein the non-aqueous solvent is non-fluorinated, and wherein the mixture of substitution products of the organic compound and elimination products of the organic compound includes equal amounts of the substitution product and the elimination product.

20. The process of claim 19, wherein the non-aqueous solvent is acetonitrile and wherein the fluoride salt is (2,2-dimethylpropyl)trimethylammonium fluoride.

21. The process of claim 18, wherein the non-aqueous solvent is fluorinated, and wherein the mixture of substitution products of the organic compound and elimination products of the organic compound includes a greater amount of the substitution product than the elimination product.

22. The process of claim 21, wherein the non-aqueous solvent is bis(2,2,2-trifluoroethyl) ether and wherein the fluoride salt is (2,2-dimethylpropyl) trimethylammonium fluoride.

* * * * *